United States Patent
Demattos et al.

(10) Patent No.: US 11,312,763 B2
(45) Date of Patent: Apr. 26, 2022

(54) ANTI-N3PGLU AMYLOID BETA PEPTIDE ANTIBODIES AND USES THEREOF

(71) Applicant: Eli Lilly and Company, Indianapolis, IN (US)

(72) Inventors: Ronald Bradley Demattos, Zionsville, IN (US); Michael Carl Irizarry, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/310,629

(22) PCT Filed: Jun. 23, 2017

(86) PCT No.: PCT/US2017/038999
§ 371 (c)(1),
(2) Date: Dec. 17, 2018

(87) PCT Pub. No.: WO2018/005282
PCT Pub. Date: Jan. 4, 2018

(65) Prior Publication Data
US 2019/0382471 A1    Dec. 19, 2019

Related U.S. Application Data

(60) Provisional application No. 62/357,579, filed on Jul. 1, 2016.

(51) Int. Cl.
*A61P 25/28* (2006.01)
*A61K 39/395* (2006.01)
*C07K 16/18* (2006.01)
*A61K 39/00* (2006.01)

(52) U.S. Cl.
CPC .......... *C07K 16/18* (2013.01); *A61K 39/3955* (2013.01); *A61P 25/28* (2018.01); *A61K 2039/545* (2013.01); *C07K 2317/24* (2013.01); *C07K 2317/92* (2013.01)

(58) Field of Classification Search
CPC .......... A61K 39/3955; A61K 2039/545; A61P 25/28; C07K 16/18; C07K 2317/92; C07K 2317/56; C07K 2317/565; C07K 2317/24
See application file for complete search history.

(56) References Cited

U.S. PATENT DOCUMENTS

| | | | |
|---|---|---|---|
| 7,122,374 B1 | 10/2006 | Saido et al. | |
| 8,613,920 B2 * | 12/2013 | Lieberburg | C07K 16/18 424/133.1 |
| 8,679,498 B2 * | 3/2014 | Lu | A61P 25/28 424/142.1 |
| 2007/0031416 A1 | 2/2007 | Asami | |
| 2008/0299111 A1 | 12/2008 | Sergeant | |
| 2010/0021478 A1 | 1/2010 | Demuth | |

FOREIGN PATENT DOCUMENTS

| | | |
|---|---|---|
| WO | 2004013172 A2 | 2/2004 |
| WO | 2006036291 A2 | 4/2006 |
| WO | 2008011348 A2 | 1/2008 |
| WO | 2009149487 A2 | 12/2009 |
| WO | 2010004434 A2 | 1/2010 |
| WO | 2010009987 A2 | 1/2010 |
| WO | 2011151076 A2 | 12/2011 |
| WO | 2012021469 A1 | 2/2012 |
| WO | 2012021475 A2 | 2/2012 |
| WO | 2015175769 A1 | 11/2015 |
| WO | 2016043997 A1 | 3/2016 |
| WO | WO-2016087944 A2 * | 6/2016 ......... A61K 39/3955 |
| WO | 2017123517 A1 | 7/2017 |
| WO | 2018005282 A1 | 1/2018 |

OTHER PUBLICATIONS

Thompson, Dennis. There's still no proven way to prevent Alzheimer's. WebMD, www.webmd.com/alzheimers/news/20171218/theres-still-no-proven-way-to-prevent-alzheimers#1; retrieved from internet on Feb. 2, 2020. (Year: 2017).*

Vickers JC A vaccine against Alzheimer's disease. Durgs Aging, 2002, 19(7):487-494. (Year: 2002).*

Oliver Wirths, et al., "Pyroglutamate Abeta pathology in APP/PS1K1 mice, sporadic and familial Alzheimer's disease cases", Journal of Neural Transmission, (2009), vol. 117(1), pp. 85-96.

Donna Wilcock, et al., Passive immunotherapy against Abeta in aged APP-transgenic mice reverses cognitive deficits and depletes parenchymal amyloid deposits in spite of increased vascular amyloid and microhemorrhage:, Journal of Neuroinflammation, (2004), vol. 1(1), p. 24.

Oliver Wirths, et al., "Identification of low molecular weight pyroglutamate Abeta oligomers in Alzheimer disease: a novel for therapy and diagnosis", Journal of Biological Chemistry, (2010), vol. 285(53), pp. 41517-41524.

David Brody, et al., "Active and passive immunotherapy for neurodegenerative disorders", Annual Review of Neuroscience, (2008), vol. 31, pp. 175-193.

Frederique Bard, et al., "Epitope and isotype specificities of antibodies to [beta]-amyloid peptide for protection against Alzheimer's disease-like neuropathy", Proc Natl Acad Science, (2003), vol. 100(4), pp. 2023-2028.

F. Luo, et al., "P2-304: MRI detection and time course of cerebral microhemorrhages during Abeta antibody treatment in living APP transgenic mice", Alzheimer's & Dementia: The Journal of the Alzheimer's Association, (2008), vol. 4(4), p. T461.

(Continued)

*Primary Examiner* — Kimberly Ballard
(74) *Attorney, Agent, or Firm* — Neelaabh Shankar

(57) ABSTRACT

The invention is directed to a short term induction treatment with anti-N3pGlu Aβ antibodies of a disease characterized by deposition of Aβ in the brain, that include Alzheimer's disease (AD), Down's syndrome, and cerebral amyloid angiopathy (CAA). In certain embodiments, patients are administered an induction dose of 10 to 60 mg/kg of an anti-N3pGlu Aβ antibody for a period of 6 months or less.

18 Claims, No Drawings
Specification includes a Sequence Listing.

(56) References Cited

OTHER PUBLICATIONS

Margaret M. Racke, et al., "Exacerbation of cerebral amyloid angiopathy-associated microhemorrhage in amyloid precursor protein transgenic mice by immunotherapy is dependent on antibody recognition of deposited forms of amyloid beta", The Journal of Neuroscience: The Office Journal of the Society for Neuroscience, (2005), vol. 25(3), pp. 629-636.

T.A. Bayer, et al., "Intraneuronal Abeta as a trigger for neuron loss: Can this be translated into human pathology?", Biochemical Society Transactions, (2011), vol. 39(4), pp. 857-861.

Desikan et al., MRI measures of temporoparietal regions show differential rates of atrophy during prodromal AD. Neurology, 2008;71:819-825.

Fennema-Notestine et al., Structural MRI Biomarkers for Preclinical and Mild Alzheimer's Disease, Human Brain Mapp. Oct. 2009; 30(10): 3238-3253.

Schroeter et al., Immunotierapy Reduces Vascular Amyloid-beta in PDAPP Mice. The Journal of Neuroscience, Jul. 2, 2008 0 28(27) :6787-6793.

DeMattos et al., A Plaque-Specific Antibody Clears Existing beta-amyloid Plaques in Alzheimer's Disease Mice. Neuron 76, 908-920, Dec. 6, 2012, 908-920.

Moro et al. Acta Neuropathologica Communications (2018) 6:3.

Anke Piechotta et al., Structural and functional analyses of pyroglutamateamyloid-amyloid-β-specific antibodies as a basis for Alzheimer immunotherapy J. Biol. Chem. (2017) 292(30) 12713-12724.

Jeffrey L Cummings, et al: "Alzheimer's disease drug-development pipeline: few candidates, frequent failures", Alzheimers Res Ther, BioMed Central LTD, London UK, vol. 6, No. 4, Jul. 3, 2014.

Sage C Arbor, et al. "Amyloid-beta Alzheimer targets—protein processing, lipid rafts, and amyloid-beta pores", The Yale Journal or biology and medicine, Mar. 1, 2016, p. 5.

Piazza, Fabrizio, et al "Amyloid-Related Imaging Abnormalities (ARIA) in Immunotherapy Trials for Alzheimer's Disease: Need for Prognostic Biomarkers?" Journal of Alzheimer's Disease, IOS Press, NL, vol. 52, No. 2, Jan. 1, 2016.

James Ferrero et al: "First-in-human, double-blind, placebo-controlled, single-dose escalation study of aducanumab (BIIB037) in mild-to-moderate Alzheimer's disease". Alzheimer's & Dementia: Translational Research & Clinical Interventions, vol. 2, No. 3, Sep. 1, 2016.

Anonymous: Single Ascending Dose Study of BIIB037 in participants with Alzheimer's Disease—Clinicaltrials.gov, (Mar. 2015).

* cited by examiner

SEQUENCE LISTING

<160> NUMBER OF SEQ ID NOS: 66

<210> SEQ ID NO 1
<211> LENGTH: 13
<212> TYPE: PRT
<213> ORGANISM: Artificial Sequence
<220> FEATURE:
<223> OTHER INFORMATION: Synthetic Construct

<400> SEQUENCE: 1

Lys Ala Ser Gly Tyr Thr Phe Thr Asp Tyr Tyr Ile Asn
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Trp Ile Asn Pro Gly Ser Gly Asn Thr Lys Tyr Asn Glu Lys Phe Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Thr Arg Glu Gly Glu Thr Val Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct

<400> SEQUENCE: 4

Lys Ser Ser Gln Ser Leu Leu Tyr Ser Arg Gly Lys Thr Tyr Leu Asn
1               5                   10                  15

```
<210> SEQ ID NO 5
<211> LENGTH: 8
<212> TYPE: PRT
<213> ORGANISM: Artificial Sequence
<220> FEATURE:
<223> OTHER INFORMATION: Synthetic Construct

<400> SEQUENCE: 5

Tyr Ala Val Ser Lys Leu Asp Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Tyr Asp Val Ser Lys Leu Asp Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Val Gln Gly Thr His Tyr Pro Phe Thr
1               5

<210> SEQ ID NO 8
<211> LENGTH: 115
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Tyr Ile Asn Trp Val Arg Gln Ala Pro Gly Gln Gly Leu Glu Trp Met
            35                  40                  45

Gly Trp Ile Asn Pro Gly Ser Gly Asn Thr Lys Tyr Asn Glu Lys Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Glu Thr Val Tyr Trp Gly Gln Gly Thr Leu Val Thr
            100                 105                 110

Val Ser Ser
        115

<210> SEQ ID NO 9
<211> LENGTH: 112
<212> TYPE: PRT
<213> ORGANISM: Artificial Sequence
<220> FEATURE:
```

<223> OTHER INFORMATION: Synthetic Construct

<400> SEQUENCE: 9

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Phe Gln Gln Arg Pro Gly Gln Ser
        35                  40                  45

Pro Arg Arg Leu Ile Tyr Asp Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110
```

<210> SEQ ID NO 10
<211> LENGTH: 112
<212> TYPE: PRT
<213> ORGANISM: Artificial Sequence
<220> FEATURE:
<223> OTHER INFORMATION: Synthetic Construct

<400> SEQUENCE: 10

```
Asp Ile Gln Met Thr Gln Ser Pro Ser Thr Leu Ser Ala Ser Val Gly
1               5                   10                  15

Asp Arg Val Thr Ile Thr Cys Lys Ser Ser Gln Ser Leu Leu Tyr Ser
            20                  25                  30

Arg Gly Lys Thr Tyr Leu Asn Trp Leu Gln Gln Lys Pro Gly Lys Ala
        35                  40                  45

Pro Lys Leu Leu Ile Tyr Ala Val Ser Lys Leu Asp Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Val Gln Gly
                85                  90                  95

Thr His Tyr Pro Phe Thr Phe Gly Gln Gly Thr Lys Leu Glu Ile Lys
            100                 105                 110
```

<210> SEQ ID NO 11
<211> LENGTH: 444
<212> TYPE: PRT
<213> ORGANISM: Artificial Sequence
<220> FEATURE:
<223> OTHER INFORMATION: Synthetic Construct

<400> SEQUENCE: 11

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
```

```
                65                  70                  75                  80
        Met Glu Leu Ser Ser Leu Arg Ser Glu Asp Thr Ala Val Tyr Tyr Cys
                        85                  90                  95

Thr Arg Glu Gly Glu Thr Val Tyr Trp Gly Gln Gly Thr Leu Val Thr
                        100                 105                 110

Val Ser Ser Ala Ser Thr Lys Gly Pro Ser Val Phe Pro Leu Ala Pro
                        115                 120                 125

Ser Ser Lys Ser Thr Ser Gly Gly Thr Ala Ala Leu Gly Cys Leu Val
                    130                 135                 140

Lys Asp Tyr Phe Pro Glu Pro Val Thr Val Ser Trp Asn Ser Gly Ala
        145                 150                 155                 160

Leu Thr Ser Gly Val His Thr Phe Pro Ala Val Leu Gln Ser Ser Gly
                            165                 170                 175

Leu Tyr Ser Leu Ser Ser Val Val Thr Val Pro Ser Ser Ser Leu Gly
                        180                 185                 190

Thr Gln Thr Tyr Ile Cys Asn Val Asn His Lys Pro Ser Asn Thr Lys
                    195                 200                 205

Val Asp Lys Lys Val Glu Pro Lys Ser Cys Asp Lys Thr His Thr Cys
                210                 215                 220

Pro Pro Cys Pro Ala Pro Glu Leu Leu Gly Gly Pro Ser Val Phe Leu
        225                 230                 235                 240

Phe Pro Pro Lys Pro Lys Asp Thr Leu Met Ile Ser Arg Thr Pro Glu
                        245                 250                 255

Val Thr Cys Val Val Val Asp Val Ser His Glu Asp Pro Glu Val Lys
                        260                 265                 270

Phe Asn Trp Tyr Val Asp Gly Val Glu Val His Asn Ala Lys Thr Lys
                    275                 280                 285

Pro Arg Glu Glu Gln Tyr Asn Ser Thr Tyr Arg Val Val Ser Val Leu
                    290                 295                 300

Thr Val Leu His Gln Asp Trp Leu Asn Gly Lys Glu Tyr Lys Cys Lys
        305                 310                 315                 320

Val Ser Asn Lys Ala Leu Pro Ala Pro Ile Glu Lys Thr Ile Ser Lys
                        325                 330                 335

Ala Lys Gly Gln Pro Arg Glu Pro Gln Val Tyr Thr Leu Pro Pro Ser
                        340                 345                 350

Arg Asp Glu Leu Thr Lys Asn Gln Val Ser Leu Thr Cys Leu Val Lys
                    355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
        385                 390                 395                 400

Ser Phe Phe Leu Tyr Ser Lys Leu Thr Val Asp Lys Ser Arg Trp Gln
                        405                 410                 415

Gln Gly Asn Val Phe Ser Cys Ser Val Met His Glu Ala Leu His Asn
                        420                 425                 430

His Tyr Thr Gln Lys Ser Leu Ser Leu Ser Pro Gly
                    435                 440

<210> SEQ ID NO 12
<211> LENGTH: 219
<212> TYPE: PRT
<213> ORGANISM: Artificial Sequence
<220> FEATURE:
<223> OTHER INFORMATION: Synthetic Construct
```

<400> SEQUENCE: 12

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Phe Gln Gln Arg Pro Gly Gln Ser
        35                  40                  45

Pro Arg Arg Leu Ile Tyr Asp Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 13
<211> LENGTH: 219
<212> TYPE: PRT
<213> ORGANISM: Artificial Sequence
<220> FEATURE:
<223> OTHER INFORMATION: Synthetic Construct

<400> SEQUENCE: 13

```
Asp Ile Gln Met Thr Gln Ser Pro Ser Thr Leu Ser Ala Ser Val Gly
1               5                   10                  15

Asp Arg Val Thr Ile Thr Cys Lys Ser Ser Gln Ser Leu Leu Tyr Ser
            20                  25                  30

Arg Gly Lys Thr Tyr Leu Asn Trp Leu Gln Gln Lys Pro Gly Lys Ala
        35                  40                  45

Pro Lys Leu Leu Ile Tyr Ala Val Ser Lys Leu Asp Ser Gly Val Pro
    50                  55                  60

Ser Arg Phe Ser Gly Ser Gly Ser Gly Thr Glu Phe Thr Leu Thr Ile
65                  70                  75                  80

Ser Ser Leu Gln Pro Asp Asp Phe Ala Thr Tyr Tyr Cys Val Gln Gly
                85                  90                  95

Thr His Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
```

```
                130                 135                 140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 14
<211> LENGTH: 1332
<212> TYPE: DNA
<213> ORGANISM: Artificial Sequence
<220> FEATURE:
<223> OTHER INFORMATION: Synthetic Construct

<400> SEQUENCE: 14
caggtgcagc tggtgcagtc tggggctgag gtgaagaagc ctgggtcctc ggtgaaggtc      60
tcctgcaagg cttctggata caccttcacc gactattata tcaactgggt gcgacaggcc     120
cctggacaag gcttgagtg gatgggatgg atcaaccctg cagtggtaa tacaaagtac       180 aatgagaagt tcaagggcag agtcacgatt accgcggacg aatccacgag cacagcctac     240
atggagctga gcagcctgag atctgaggac acggccgtgt attactgtac aagagaaggc     300
gagacggtct actggggcca gggaaccctg gtcaccgtct cctcagcctc caccaagggc     360
ccatcggtct tccccgctag cacctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaactcctgg ggggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca agccctccc agcccccatc gagaaaacca tctccaaagc caaagggcag    1020 cccccgagaac cacaggtgta caccctgccc ccatcccggg acgagctgac caagaaccag    1080
gtcagcctga cctgcctggt caaaggcttc tatcccagcg acatcgccgt ggagtgggag    1140
agcaatgggc agccggagaa caactacaag accacgcccc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gt                                                       1332

<210> SEQ ID NO 15
<211> LENGTH: 657
<212> TYPE: DNA
<213> ORGANISM: Artificial Sequence
<220> FEATURE:
```

<223> OTHER INFORMATION: Synthetic Construct

<400> SEQUENCE: 15

```
gatgttgtga tgactcagtc tccactctcc ctgcccgtca cccttggaca gccggcctcc    60
atctcctgca gtctagtca aagcctcctg tacagtcgcg aaaaaccta cttgaattgg    120
tttcagcaga ggccaggcca atctccaagg cgcctaattt atgatgtttc taaactggac    180
tctggggtcc cagacagatt cagcggcagt gggtcaggca ctgatttcac actgaaaatc    240
agcagggtgg aggctgagga tgttgggggtt tattactgcg tgcaaggtac acactaccct    300
ttcacttttg gccaagggac caagctggag atcaaacgga ccgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacagggg agagtgc    657
```

<210> SEQ ID NO 16
<211> LENGTH: 657
<212> TYPE: DNA
<213> ORGANISM: Artificial Sequence
<220> FEATURE:
<223> OTHER INFORMATION: Synthetic Construct

<400> SEQUENCE: 16

```
gacatccaga tgacccagtc tccttccacc ctgtctgcat ctgtaggaga cagagtcacc    60
atcacttgca gtccagtca gagtctcctg tacagtcgcg aaaaaccta tttgaactgg    120
ctccagcaga accagggaa agcccctaag ctcctgatct atgctgtctc caaactggac    180
agtggggtcc catcaaggtt cagcggcagt ggatctggga cagaattcac tctcaccatc    240
agcagcctgc agcctgatga ttttgcaact tattactgcg tgcagggtac acattatcct    300
ttcacttttg gccaggggac caagctggag atcaaacgga ccgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacagggg agagtgc    657
```

<210> SEQ ID NO 17
<211> LENGTH: 16
<212> TYPE: PRT
<213> ORGANISM: Artificial Sequence
<220> FEATURE:
<223> OTHER INFORMATION: Synthetic Construct

<400> SEQUENCE: 17

Lys Ser Ser Gln Ser Leu Leu Tyr Ser Arg Gly Lys Thr Tyr Leu Asn
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 18

Ala Val Ser Lys Leu Asp Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Val Gln Gly Thr His Tyr Pro Phe Thr
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Gly Tyr Asp Phe Thr Arg Tyr Tyr Ile Asn
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Gly Tyr Thr Phe Thr Arg Tyr Tyr Ile Asn
1               5                   10

<210> SEQ ID NO 22
<211> LENGTH: 17
<212> TYPE: PRT
<213> ORGANISM: Artificial Sequence
<220> FEATURE:
<223> OTHER INFORMATION: Synthetic Construct

<400> SEQUENCE: 22

Trp Ile Asn Pro Gly Ser Gly Asn Thr Lys Tyr Asn Glu Lys Phe Lys
1               5                   10                  15

Gly

<210> SEQ ID NO 23
<211> LENGTH: 6
<212> TYPE: PRT
<213> ORGANISM: Artificial Sequence
<220> FEATURE:
<223> OTHER INFORMATION: Synthetic Construct

<400> SEQUENCE: 23

Glu Gly Ile Thr Val Tyr
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Construct
```

<400> SEQUENCE: 24

Glu Gly Thr Thr Val Tyr
1               5

<210> SEQ ID NO 25
<211> LENGTH: 112
<212> TYPE: PRT
<213> ORGANISM: Artificial Sequence
<220> FEATURE:
<223> OTHER INFORMATION: Synthetic Construct

<400> SEQUENCE: 25

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Leu Leu Gln Lys Pro Gly Gln Ser
        35                  40                  45

Pro Gln Leu Leu Ile Tyr Ala Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

<210> SEQ ID NO 26
<211> LENGTH: 115
<212> TYPE: PRT
<213> ORGANISM: Artificial Sequence
<220> FEATURE:
<223> OTHER INFORMATION: Synthetic Construct

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Thr Arg Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ile Thr Val Tyr Trp Gly Gln Gly Thr Thr Val Thr
            100                 105                 110

Val Ser Ser
        115

<210> SEQ ID NO 27
<211> LENGTH: 115
<212> TYPE: PRT
<213> ORGANISM: Artificial Sequence
<220> FEATURE:
<223> OTHER INFORMATION: Synthetic Construct

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Tyr
                20                  25                  30

Tyr Ile Asn Trp Val Arg Gln Ala Pro Gly Gln Gly Leu Glu Trp Met
            35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Thr Val Tyr Trp Gly Gln Gly Thr Thr Val Thr
            100                 105                 110

Val Ser Ser
        115

<210> SEQ ID NO 28
<211> LENGTH: 219
<212> TYPE: PRT
<213> ORGANISM: Artificial Sequence
<220> FEATURE:
<223> OTHER INFORMATION: Synthetic Construct

<400> SEQUENCE: 28

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
                20                  25                  30

Arg Gly Lys Thr Tyr Leu Asn Trp Leu Leu Gln Lys Pro Gly Gln Ser
            35                  40                  45

Pro Gln Leu Leu Ile Tyr Ala Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 29
<211> LENGTH: 444
<212> TYPE: PRT
<213> ORGANISM: Artificial Sequence
<220> FEATURE:
<223> OTHER INFORMATION: Synthetic Construct

<400> SEQUENCE: 29

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Thr Arg Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
50                  55                  60

Lys Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ile Thr Val Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
```

```
            370                 375                 380
Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
                435                 440

<210> SEQ ID NO 30
<211> LENGTH: 444
<212> TYPE: PRT
<213> ORGANISM: Artificial Sequence
<220> FEATURE:
<223> OTHER INFORMATION: Synthetic Construct

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Tyr
                20                  25                  30

Tyr Ile Asn Trp Val Arg Gln Ala Pro Gly Gln Gly Leu Glu Trp Met
            35                  40                  45

Gly Trp Ile Asn Pro Gly Ser Gly Asn Thr Lys Tyr Asn Glu Lys Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Thr Val Tyr Trp Gly Gln Gly Thr Thr Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
```

```
                290                 295                 300
Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
            435                 440

<210> SEQ ID NO 31
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 = pyroglutamic acid

<400> SEQUENCE: 31

Xaa Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
                20                  25                  30

Met Val Gly Gly Val Val Ile Ala
            35                  40

<210> SEQ ID NO 32
<211> LENGTH: 112
<212> TYPE: PRT
<213> ORGANISM: Artificial Sequence
<220> FEATURE:
<223> OTHER INFORMATION: Synthetic Construct

<400> SEQUENCE: 32

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
                20                  25                  30

Arg Gly Lys Thr Tyr Leu Asn Trp Leu Leu Gln Lys Pro Gly Gln Ser
            35                  40                  45

Pro Gln Leu Leu Ile Tyr Ala Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95
```

```
Thr His Tyr Pro Phe Thr Phe Gly Gln Gly Thr Lys Leu Glu Ile Lys
                100                 105                 110

<210> SEQ ID NO 33
<211> LENGTH: 219
<212> TYPE: PRT
<213> ORGANISM: Artificial Sequence
<220> FEATURE:
<223> OTHER INFORMATION: Synthetic Construct

<400> SEQUENCE: 33

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Leu Leu Gln Lys Pro Gly Gln Ser
        35                  40                  45

Pro Gln Leu Leu Ile Tyr Ala Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 34
<211> LENGTH: 115
<212> TYPE: PRT
<213> ORGANISM: Artificial Sequence
<220> FEATURE:
<223> OTHER INFORMATION: Synthetic Construct

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
```

```
65                  70                  75                  80
Met Glu Leu Ser Ser Leu Arg Ser Glu Asp Thr Ala Val Tyr Tyr Cys
                85                  90                  95

Ala Arg Glu Gly Glu Thr Val Tyr Trp Gly Gln Gly Thr Thr Val Thr
            100                 105                 110

Val Ser Ser
        115

<210> SEQ ID NO 35
<211> LENGTH: 444
<212> TYPE: PRT
<213> ORGANISM: Artificial Sequence
<220> FEATURE:
<223> OTHER INFORMATION: Synthetic Construct

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
            35                  40                  45

Gly Trp Ile Asn Pro Gly Ser Gly Asn Thr Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Thr Val Tyr Trp Gly Gln Gly Thr Thr Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
```

```
                305                 310                 315                 320
Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
            435                 440

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Gly Tyr Thr Phe Thr Asp Tyr Tyr Ile Asn
1               5                   10

<210> SEQ ID NO 37
<211> LENGTH: 6
<212> TYPE: PRT
<213> ORGANISM: Artificial Sequence
<220> FEATURE:
<223> OTHER INFORMATION: Synthetic Construct

<400> SEQUENCE: 37

Glu Gly Glu Thr Val Tyr
1               5

<210> SEQ ID NO 38
<211> LENGTH: 42
<212> TYPE: PRT
<213> ORGANISM: Artificial Sequence
<220> FEATURE:
<223> OTHER INFORMATION: Synthetic Construct

<400> SEQUENCE: 38

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 39
<211> LENGTH: 145
<212> TYPE: PRT
<213> ORGANISM: Artificial Sequence
<220> FEATURE:
<223> OTHER INFORMATION: Synthetic Construct
```

-continued

```
<400> SEQUENCE: 39

Met Val Ser Ser Ala Gln Phe Leu Phe Leu Val Leu Trp Ile Gln
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Tyr Ser Asp Gly Lys Thr Tyr Leu Asn Trp Leu Leu Gln Arg
    50                  55                  60

Pro Gly Gln Ser Pro Met Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Val Gln Gly Thr His Phe Pro Phe Thr Phe Gly Ser Gly Thr Lys
        115                 120                 125

Leu Glu Ile Lys Arg Ala Asp Ala Ala Pro Thr Val Ser Ile Phe Pro
    130                 135                 140

Pro
145

<210> SEQ ID NO 40
<211> LENGTH: 146
<212> TYPE: PRT
<213> ORGANISM: Artificial Sequence
<220> FEATURE:
<223> OTHER INFORMATION: Synthetic Construct

<400> SEQUENCE: 40

Met Gly Trp Ser Gly Val Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Lys Asn Leu
    50                  55                  60

Glu Trp Ile Gly Leu Ile Asn Pro Tyr Ser Gly Val Thr Arg Tyr Asn
65                  70                  75                  80

Gln Lys Phe Lys Gly Lys Ala Thr Leu Ile Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Thr Arg Glu Ala Lys Arg Glu Trp Asp Glu Thr Tyr Trp
        115                 120                 125

Gly Gln Gly Thr Leu Val Thr Val Ser Ala Ala Lys Thr Thr Pro Pro
    130                 135                 140

Ser Val
145

<210> SEQ ID NO 41
<211> LENGTH: 146
<212> TYPE: PRT
<213> ORGANISM: Artificial Sequence
<220> FEATURE:
<223> OTHER INFORMATION: Synthetic Construct
```

<400> SEQUENCE: 41

Met Val Ser Thr Ala Gln Phe Leu Phe Leu Leu Val Leu Trp Ile Gln
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Tyr Ser Asp Gly Lys Thr Tyr Leu Asn Trp Leu Leu Gln Arg
    50                  55                  60

Pro Gly Gln Ser Pro Met Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Val Gln Gly Thr His Phe Pro Phe Thr Phe Gly Ser Gly Thr Lys
        115                 120                 125

Leu Glu Ile Lys Arg Ala Asp Ala Ala Pro Thr Val Ser Ile Phe Pro
    130                 135                 140

Pro Ser
145

<210> SEQ ID NO 42
<211> LENGTH: 149
<212> TYPE: PRT
<213> ORGANISM: Artificial Sequence
<220> FEATURE:
<223> OTHER INFORMATION: Synthetic Construct

<400> SEQUENCE: 42

Met Gly Trp Ser Gly Val Phe Ile Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Lys Asn Leu
    50                  55                  60

Glu Trp Ile Gly Leu Ile Asn Pro Tyr Asn Gly Val Thr Arg Tyr Asn
65                  70                  75                  80

Gln Lys Phe Lys Gly Lys Ala Thr Leu Ile Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Thr Arg Glu Ala Lys Arg Glu Trp Asp Glu Thr Tyr Trp
        115                 120                 125

Gly Gln Gly Thr Leu Val Thr Val Ser Ala Ala Lys Thr Thr Pro Pro
    130                 135                 140

Ser Val Tyr Pro Leu
145

<210> SEQ ID NO 43
<211> LENGTH: 146
<212> TYPE: PRT
<213> ORGANISM: Artificial Sequence
<220> FEATURE:

<223> OTHER INFORMATION: Synthetic Construct

<400> SEQUENCE: 43

Met Lys Leu Pro Val Arg Leu Leu Val Leu Phe Trp Ile Pro Val
1               5                   10                  15

Ser Ser Ser Asp Val Val Met Thr Gln Thr Pro Leu Ser Leu Pro Val
                20                  25                  30

Ser Leu Gly Asp Gln Ala Ser Ile Ser Cys Arg Ser Ser Gln Ser Leu
            35                  40                  45

Val His Ser Asp Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Pro Thr Phe Gly Gly Gly Thr Lys Leu
        115                 120                 125

Glu Ile Lys Arg Ala Asp Ala Ala Pro Thr Val Ser Ile Phe Pro Pro
130                 135                 140

Ser Ser
145

<210> SEQ ID NO 44
<211> LENGTH: 152
<212> TYPE: PRT
<213> ORGANISM: Artificial Sequence
<220> FEATURE:
<223> OTHER INFORMATION: Synthetic Construct

<400> SEQUENCE: 44

Met Asp Phe Gly Leu Ser Leu Leu Ile Phe Val Leu Ile Leu Lys Gly
1               5                   10                  15

Val Gln Cys Glu Val Lys Leu Val Glu Ser Gly Gly Gly Leu Val Gln
                20                  25                  30

Pro Gly Gly Ser Arg Lys Leu Ser Cys Ala Ala Ser Gly Phe Thr Phe
            35                  40                  45

Ser Asp Tyr Gly Met Ala Trp Val Arg Gln Ala Pro Gly Lys Gly Pro
    50                  55                  60

Glu Trp Val Ala Phe Ile Ser Asn Leu Ala Tyr Ser Ile Tyr Tyr Ala
65                  70                  75                  80

Asp Thr Val Thr Gly Arg Phe Thr Ile Ser Arg Glu Asn Ala Lys Asn
                85                  90                  95

Thr Leu Tyr Leu Glu Met Ser Ser Leu Arg Ser Glu Asp Thr Ala Met
            100                 105                 110

Tyr Tyr Cys Ala Arg Tyr Asp Tyr Asp Asn Ile Leu Asp Tyr Val Met
        115                 120                 125

Asp Tyr Trp Gly Gln Gly Thr Ser Val Thr Val Ser Ser Ala Lys Thr
130                 135                 140

Thr Pro Pro Ser Val Tyr Pro Leu
145                 150

<210> SEQ ID NO 45
<211> LENGTH: 144
<212> TYPE: PRT
<213> ORGANISM: Artificial Sequence

```
<220> FEATURE:
<223> OTHER INFORMATION: Synthetic Construct

<400> SEQUENCE: 45

Met Lys Leu Pro Val Arg Leu Leu Val Leu Trp Ile Gln Glu Thr Lys
1               5                   10                  15

Gly Asp Val Val Leu Thr Gln Thr Pro Leu Thr Leu Ser Val Thr Ile
                20                  25                  30

Gly Gln Pro Ala Ser Ile Ser Cys Lys Ser Ser Gln Ser Leu Leu Tyr
            35                  40                  45

Ser Asn Gly Lys Thr Tyr Leu Asn Trp Leu Leu Gln Arg Pro Gly Gln
        50                  55                  60

Ser Pro Lys Arg Leu Ile Tyr Val Val Ser Lys Leu Asp Ser Gly Val
65                  70                  75                  80

Pro Asp Arg Phe Thr Gly Ser Gly Ser Gly Thr Asp Phe Thr Leu Lys
                85                  90                  95

Ile Ser Arg Val Glu Ala Glu Asp Leu Gly Val Tyr Tyr Cys Val Gln
            100                 105                 110

Gly Thr His Phe Pro Phe Thr Phe Gly Ser Gly Thr Lys Leu Glu Ile
        115                 120                 125

Lys Arg Ala Asp Ala Ala Pro Thr Val Ser Ile Phe Pro Pro Ser Ser
    130                 135                 140

<210> SEQ ID NO 46
<211> LENGTH: 145
<212> TYPE: PRT
<213> ORGANISM: Artificial Sequence
<220> FEATURE:
<223> OTHER INFORMATION: Synthetic Construct

<400> SEQUENCE: 46

Met Gly Trp Ser Gly Val Phe Leu Phe Leu Leu Ser Val Thr Glu Gly
1               5                   10                  15

Val His Ser Gln Val Gln Leu Gln Gln Ser Gly Ala Glu Leu Val Arg
                20                  25                  30

Pro Gly Ser Ser Val Lys Ile Ser Cys Lys Ala Ser Gly Tyr Ile Phe
            35                  40                  45

Asn Asn Tyr Trp Ile Asn Trp Val Lys Gln Arg Pro Gly Gln Gly Leu
        50                  55                  60

Glu Trp Ile Gly Gln Ile Tyr Pro Gly Asp Gly Asp Thr Asn Tyr Asn
65                  70                  75                  80

Gly Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Glu Gly Tyr Ile Val Tyr Trp Gly Gln Gly Thr
        115                 120                 125

Leu Val Thr Val Ser Ala Ala Lys Thr Thr Pro Pro Ser Val Tyr Pro
    130                 135                 140

Leu
145

<210> SEQ ID NO 47
<211> LENGTH: 107
<212> TYPE: PRT
<213> ORGANISM: Artificial Sequence
<220> FEATURE:
<223> OTHER INFORMATION: Synthetic Construct
```

<400> SEQUENCE: 47

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr
            100                 105

<210> SEQ ID NO 48
<211> LENGTH: 115
<212> TYPE: PRT
<213> ORGANISM: Artificial Sequence
<220> FEATURE:
<223> OTHER INFORMATION: Synthetic Construct

<400> SEQUENCE: 48

Gln Leu Gln Gln Ser Gly Ala Glu Leu Met Lys Pro Gly Ala Ser Val
1               5                   10                  15

Lys Ile Ser Cys Lys Ala Thr Gly Tyr Thr Phe Ser Ser Tyr Trp Ile
            20                  25                  30

Glu Trp Val Lys Gln Arg Pro Gly His Gly Leu Glu Trp Ile Gly Glu
        35                  40                  45

Ile Leu Pro Gly Arg Gly Ser Thr His Tyr Asn Glu Lys Phe Lys Gly
    50                  55                  60

Lys Ala Thr Phe Thr Ala Asp Thr Ser Ser Asn Thr Ala Tyr Met Gln
65                  70                  75                  80

Leu Ser Ser Leu Thr Ser Glu Asp Ser Ala Val Tyr Tyr Cys Ala Arg
                85                  90                  95

Ser Pro Ile Thr Thr Ser Asp Tyr Trp Gly Gln Gly Thr Thr Leu Thr
            100                 105                 110

Val Ser Ser
        115

<210> SEQ ID NO 49
<211> LENGTH: 86
<212> TYPE: PRT
<213> ORGANISM: Artificial Sequence
<220> FEATURE:
<223> OTHER INFORMATION: Synthetic Construct

<400> SEQUENCE: 49

Ser Cys Arg Ser Ser Gln Ser Leu Val His Ser Asn Gly Asn Thr Tyr
1               5                   10                  15

Leu His Trp Tyr Leu Gln Lys Pro Gly Gln Ser Pro Lys Leu Leu Ile
            20                  25                  30

Tyr Lys Val Ser Asn Arg Phe Ser Gly Val Pro Asp Arg Phe Ser Gly
        35                  40                  45

Ser Gly Ser Gly Thr Asp Phe Thr Leu Lys Ile Ser Arg Val Glu Ala
    50                  55                  60

Glu Asp Leu Gly Val Tyr Phe Cys Ser Gln Ser Thr His Val Pro Leu
65                  70                  75                  80

Thr Phe Gly Ala Gly Thr
                85

<210> SEQ ID NO 50
<211> LENGTH: 98
<212> TYPE: PRT
<213> ORGANISM: Artificial Sequence
<220> FEATURE:
<223> OTHER INFORMATION: Synthetic Construct

<400> SEQUENCE: 50

Ala Glu Leu Lys Lys Pro Gly Ala Ser Val Lys Ile Ser Cys Lys Ala
1               5                   10                  15

Thr Gly Tyr Thr Phe Arg Ser Tyr Trp Ile Glu Trp Val Lys Gln Arg
            20                  25                  30

Pro Gly His Gly Leu Glu Trp Ile Gly Glu Ile Leu Pro Gly Arg Gly
        35                  40                  45

Ser Thr Lys Tyr Asn Glu Lys Phe Lys Gly Lys Ala Thr Phe Thr Ala
    50                  55                  60

Asp Thr Ser Ser Asn Thr Ala Asn Met Gln Leu Ser Ser Leu Thr Ser
65                  70                  75                  80

Glu Asp Ser Ala Val Tyr Tyr Cys Ala Arg Ser Pro Ile Thr Thr Ser
                85                  90                  95

Asp Tyr

<210> SEQ ID NO 51
<211> LENGTH: 112
<212> TYPE: PRT
<213> ORGANISM: Artificial Sequence
<220> FEATURE:
<223> OTHER INFORMATION: Synthetic Construct

<400> SEQUENCE: 51

Asp Val Val Leu Thr Gln Thr Pro Phe Thr Leu Ser Val Thr Ile Gly
1               5                   10                  15

Gln Pro Ala Ser Ile Ser Cys Lys Ser Ser Gln Ser Leu Leu His Ser
            20                  25                  30

Asn Gly Glu Ser Tyr Leu Asn Trp Leu Phe Gln Arg Pro Gly Gln Ser
        35                  40                  45

Pro Lys Arg Leu Ile Tyr Ala Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Phe Thr Phe Gly Gly Gly Thr Lys Leu Glu Ile Lys
            100                 105                 110

<210> SEQ ID NO 52
<211> LENGTH: 115
<212> TYPE: PRT
<213> ORGANISM: Artificial Sequence
<220> FEATURE:
<223> OTHER INFORMATION: Synthetic Construct

<400> SEQUENCE: 52

Gln Ile Gln Leu Gln Gln Ser Gly Pro Glu Leu Val Lys Pro Gly Ala

```
            1               5                  10                 15
          Ala Val Lys Ile Ser Cys Lys Ala Ser Gly Tyr Thr Phe Thr Asp Tyr
                          20                  25                 30

Tyr Leu Asn Trp Val Lys Gln Lys Pro Gly Gln Gly Leu Glu Trp Ile
                          35                  40                 45

Gly Trp Ile Tyr Pro Gly Ser Gly Asn Val Lys Tyr Asn Glu Lys Phe
                  50                  55                  60

Lys Gly Lys Ala Thr Leu Thr Ala Asp Thr Ser Ser Asn Thr Ala His
           65                  70                  75                  80

Met Gln Leu Ser Ser Leu Thr Ser Glu Asp Thr Ala Val Tyr Phe Cys
                          85                  90                  95

Thr Arg Glu Gly Leu Ile Val Tyr Trp Gly Gln Gly Thr Leu Val Thr
                          100                 105                110

Val Ser Ala
                  115

<210> SEQ ID NO 53
<211> LENGTH: 112
<212> TYPE: PRT
<213> ORGANISM: Artificial Sequence
<220> FEATURE:
<223> OTHER INFORMATION: Synthetic Construct

<400> SEQUENCE: 53

Asp Val Val Leu Thr Gln Thr Pro Leu Thr Leu Ser Val Thr Ile Gly
           1               5                  10                 15

Gln Pro Ala Ser Ile Ser Cys Lys Ser Ser Gln Ser Leu Leu Tyr Ser
                          20                  25                 30

Asn Gly Lys Thr Tyr Leu Asn Trp Leu Leu Gln Arg Pro Gly Gln Ser
                          35                  40                 45

Pro Lys Arg Leu Ile Tyr Val Val Ser Lys Leu Asp Ser Gly Val Pro
                  50                  55                  60

Asp Arg Phe Thr Gly Ser Gly Ser Gly Thr Asp Phe Thr Leu Lys Ile
           65                  70                  75                  80

Ser Arg Val Glu Ala Glu Asp Leu Gly Val Tyr Tyr Cys Val Gln Gly
                          85                  90                  95

Thr His Tyr Pro Phe Thr Phe Gly Gly Gly Thr Lys Leu Glu Ile Lys
                          100                 105                110

<210> SEQ ID NO 54
<211> LENGTH: 115
<212> TYPE: PRT
<213> ORGANISM: Artificial Sequence
<220> FEATURE:
<223> OTHER INFORMATION: Synthetic Construct

<400> SEQUENCE: 54

Gln Ile Gln Leu Gln Gln Ser Gly Pro Asp Leu Val Lys Pro Gly Ala
           1               5                  10                 15

Ser Val Lys Ile Ser Cys Lys Ala Ser Gly Tyr Thr Phe Thr Asp Tyr
                          20                  25                 30

Tyr Ile Asn Trp Val Lys Gln Lys Pro Gly Gln Gly Leu Glu Trp Ile
                          35                  40                 45

Gly Trp Leu Asn Pro Gly Ser Gly Asn Thr Lys Tyr Asn Glu Lys Phe
                  50                  55                  60

Lys Gly Lys Ala Thr Met Thr Val Asp Thr Ser Ser Ser Thr Val Tyr
           65                  70                  75                  80
```

```
Met Gln Leu Ser Ser Leu Thr Ser Glu Asp Ser Ala Val Tyr Phe Cys
                85                  90                  95

Thr Arg Glu Gly Pro Ile Asp Tyr Trp Gly Arg Gly Thr Ser Val Thr
            100                 105                 110

Val Ser Ser
        115

<210> SEQ ID NO 55
<211> LENGTH: 112
<212> TYPE: PRT
<213> ORGANISM: Artificial Sequence
<220> FEATURE:
<223> OTHER INFORMATION: Synthetic Construct

<400> SEQUENCE: 55

Asp Ile Val Met Thr Gln Thr Pro Leu Ser Leu Ser Val Thr Pro Gly
1               5                   10                  15

Gln Pro Ala Ser Ile Ser Cys Ser Ser Ser Gln Ser Leu Ile Tyr Ser
            20                  25                  30

Asp Gly Asn Ala Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Thr Gln Ser
                85                  90                  95

Thr His Ser Pro Trp Thr Phe Gly Gly Gly Thr Lys Val Glu Ile Lys
            100                 105                 110

<210> SEQ ID NO 56
<211> LENGTH: 112
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Ser Arg Tyr
            20                  25                  30

Ser Met Ser Trp Val Arg Gln Ala Pro Gly Lys Gly Leu Glu Trp Val
        35                  40                  45

Gly Gln Ile Asn Ile Arg Gly Cys Asn Thr Tyr Tyr Pro Asp Thr Val
    50                  55                  60

Lys Gly Arg Phe Thr Ile Ser Arg Asp Asp Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Gly Asp Phe Trp Gly Gln Gly Thr Leu Val Thr Val Ser Ser
            100                 105                 110

<210> SEQ ID NO 57
<211> LENGTH: 214
<212> TYPE: PRT
<213> ORGANISM: Artificial Sequence
<220> FEATURE:
<223> OTHER INFORMATION: Synthetic Construct
```

<400> SEQUENCE: 57

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 58
<211> LENGTH: 453
<212> TYPE: PRT
<213> ORGANISM: Artificial Sequence
<220> FEATURE:
<223> OTHER INFORMATION: Synthetic Construct

<400> SEQUENCE: 58

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Thr Lys Lys Tyr Tyr Thr Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Arg Asp Arg Gly Ile Gly Ala Arg Arg Gly Pro Tyr Tyr Met Asp
            100                 105                 110

Val Trp Gly Lys Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
```

```
                130                 135                 140
Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 59
<211> LENGTH: 215
<212> TYPE: PRT
<213> ORGANISM: Artificial Sequence
<220> FEATURE:
<223> OTHER INFORMATION: Synthetic Construct

<400> SEQUENCE: 59

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
```

```
                 35                  40                  45
Ile Tyr Gly Ala Ser Ser Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Leu Gln Ile Tyr Asn Met Pro
                 85                  90                  95

Ile Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 60
<211> LENGTH: 456
<212> TYPE: PRT
<213> ORGANISM: Artificial Sequence
<220> FEATURE:
<223> OTHER INFORMATION: Synthetic Construct

<400> SEQUENCE: 60

Gln Val Glu Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Asn Ala Ser Gly Thr Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Lys Gly Asn Thr His Lys Pro Tyr Gly Tyr Val Arg Tyr
                100                 105                 110

Phe Asp Val Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
```

```
            180                 185                 190
Ser Val Val Thr Val Pro Ser Ser Leu Gly Thr Gln Thr Tyr Ile
            195                 200                 205
Cys Asn Val Asn His Lys Pro Ser Asn Thr Lys Val Asp Lys Lys Val
            210                 215             220
Glu Pro Lys Ser Cys Asp Lys Thr His Thr Cys Pro Pro Cys Pro Ala
225                 230                 235                 240
Pro Glu Leu Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser His Glu Asp Pro Glu Val Lys Phe Asn Trp Tyr Val
            275                 280                 285
Asp Gly Val Glu Val His Asn Ala Lys Thr Lys Pro Arg Glu Glu Gln
            290                 295                 300
Tyr Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Ser Arg Asp Glu Leu Thr
            355                 360                 365
Lys Asn Gln Val Ser Leu Thr Cys Leu Val Lys Gly Phe Tyr Pro Ser
            370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
            435                 440                 445
Ser Leu Ser Leu Ser Pro Gly Lys
            450                 455

<210> SEQ ID NO 61
<211> LENGTH: 219
<212> TYPE: PRT
<213> ORGANISM: Artificial Sequence
<220> FEATURE:
<223> OTHER INFORMATION: Synthetic Construct

<400> SEQUENCE: 61

Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Val Tyr Ser
            20                  25                  30
Asn Gly Asp Thr Tyr Leu His Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ser Gln Ser
```

```
                  85                  90                  95
Thr His Val Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 62
<211> LENGTH: 438
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Gly Met Ser Trp Val Arg Gln Ala Pro Gly Lys Gly Leu Glu Leu Val
                35                  40                  45

Ala Ser Ile Asn Ser Asn Gly Gly Ser Thr Tyr Tyr Pro Asp Ser Val
                50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
                100                 105                 110

Ala Ser Thr Lys Gly Pro Ser Val Phe Pro Leu Ala Pro Cys Ser Arg
                115                 120                 125

Ser Thr Ser Glu Ser Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
                180                 185                 190

Tyr Thr Cys Asn Val Asp His Lys Pro Ser Asn Thr Lys Val Asp Lys
                195                 200                 205

Arg Val Glu Ser Lys Tyr Gly Pro Pro Cys Pro Pro Cys Pro Ala Pro
                210                 215                 220

Glu Phe Leu Gly Gly Pro Ser Val Phe Leu Phe Pro Pro Lys Pro Lys
```

```
                225                 230                 235                 240
Asp Thr Leu Met Ile Ser Arg Thr Pro Glu Val Thr Cys Val Val Val
                    245                 250                 255

Asp Val Ser Gln Glu Asp Pro Glu Val Gln Phe Asn Trp Tyr Val Asp
                260                 265                 270

Gly Val Glu Val His Asn Ala Lys Thr Lys Pro Arg Glu Glu Gln Phe
                275                 280                 285

Asn Ser Thr Tyr Arg Val Val Ser Val Leu Thr Val Leu His Gln Asp
            290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
                340                 345                 350

Asn Gln Val Ser Leu Thr Cys Leu Val Lys Gly Phe Tyr Pro Ser Asp
                355                 360                 365

Ile Ala Val Glu Trp Glu Ser Asn Gly Gln Pro Glu Asn Asn Tyr Lys
            370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
                420                 425                 430

Leu Ser Leu Ser Leu Gly
            435

<210> SEQ ID NO 63
<211> LENGTH: 219
<212> TYPE: PRT
<213> ORGANISM: Artificial Sequence
<220> FEATURE:
<223> OTHER INFORMATION: Synthetic Construct

<400> SEQUENCE: 63

Asp Val Val Met Thr Gln Ser Pro Leu Ser Leu Pro Val Thr Pro Gly
1               5                   10                  15

Ala Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Phe Gln Gly
                85                  90                  95

Ser His Val Pro Pro Thr Phe Gly Pro Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
```

```
                  145                 150                 155                 160
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 64
<211> LENGTH: 454
<212> TYPE: PRT
<213> ORGANISM: Artificial Sequence
<220> FEATURE:
<223> OTHER INFORMATION: Synthetic Construct

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Ala Tyr Ile Ser Ser Gly Ser Ser Thr Ile Tyr Tyr Gly Asp Thr Val
        50                  55                  60

Lys Gly Arg Phe Thr Ile Ser Arg Asp Asn Ala Lys Asn Ser Leu Phe
65                  70                  75                  80

Leu Gln Met Ser Ser Leu Arg Ala Glu Asp Thr Ala Val Tyr Tyr Cys
                85                  90                  95

Ala Arg Glu Gly Gly Tyr Tyr Gly Arg Ser Tyr Tyr Thr Met Asp
                100                 105                 110

Tyr Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Arg Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
```

```
            290                 295                 300
Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 65
<211> LENGTH: 219
<212> TYPE: PRT
<213> ORGANISM: Artificial Sequence
<220> FEATURE:
<223> OTHER INFORMATION: Synthetic Construct

<400> SEQUENCE: 65

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

```
            195                 200                 205
Pro Val Thr Lys Ser Phe Asn Arg Gly Glu Cys
    210                 215
```

<210> SEQ ID NO 66
<211> LENGTH: 442
<212> TYPE: PRT
<213> ORGANISM: Artificial Sequence
<220> FEATURE:
<223> OTHER INFORMATION: Synthetic Construct

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Leu Val
        35                  40                  45

Ala Gln Ile Asn Ser Val Gly Asn Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
```

```
                    340                 345                 350
Leu Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
        370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
            435                 440
```

ANTI-N3PGLU AMYLOID BETA PEPTIDE ANTIBODIES AND USES THEREOF

The present invention relates to treatment of a disease with anti-N3pGlu Aβ antibodies, wherein the disease is characterized by deposition of Amyloid Beta (Aβ) in a patient. More specifically, the present invention relates to a short term induction treatment with N3pGlu Aβ antibodies of a disease characterized by deposition of A in m the brain, including Alzheimer's disease (AD), Down's syndrome, and cerebral amyloid angiopathy (CAA).

The deposits found in plaques of human patients are comprised of a heterogeneous mixture of Aβ peptides. N3pGlu Aβ, also referred to as N3pE Aβ, Aβ pE3-42, or $Aβ_{p3-42}$, is a truncated form of Aβ peptide and is found only in plaques. N3pGlu Aβ lacks the first two amino acid residues at the N-terminus of human Aβ and has a pyroglutamate which was derived from the glutamic acid at the third amino acid position. Although N3pGlu AB peptide is a minor component of the deposited Aβ in the brain, studies have demonstrated that N3pGlu Aβ peptide has aggressive aggregation properties and accumulates early in the deposition cascade.

Antibodies to N3pGlu Aβ are known in the art. For example, U.S. Pat. No. 8,679,498 discloses anti-N3pGlu Aβ antibodies and methods of treating diseases such as Alzheimer's disease, with the antibodies. Passive immunization by long term chronic administration of antibodies against the Aβ, including N3pGlu Aβ, found in deposits has been shown to disrupt the Aβ aggregates and promote the clearance of plaques in the brain in various animal models. However, in humans long term chronic administration of Aβ antibodies has led to adverse events that include amyloid-related imaging abnormalities (ARIA), suggestive of vasogenic edema and sulcal effusions (ARIA-E), as well as microhemorrhages and haemosiderin deposits (ARIA-H) as well as infusion site reactions and risk of immunogenicity. See Piazza and Winblad. "Amyloid-Related Imaging Abnormalities (ARIA) in Immunotherapy Trials for Alzheimer's Disease: Need for Prognostic Biomarkers?" Journal of Alzheimer's Disease, 52 (2016) 417-420.

The present invention overcomes the problems associated with long term chronic administration. Applicants found that short term induction treatment with relatively high doses of anti-N3pGlu Aβ antibodies promotes significant clearance of plaques in the brain of patients with AB deposits, and this clearance is surprisingly maintained for an extended period of time. The short term induction treatment can include a one-time dose of an anti-N3pGlu antibody, a biweekly dose of an anti-N3pGlu Aβ antibody for a period of 6 months, or a monthly dose of an anti-N3pGlu Aβ antibody for a period of 6 months or less. In addition to reducing the adverse events caused by long term chronic dosing of antibodies against Aβ, additional benefits of the short term induction treatment include improved patient compliance, reduced infusion site reactions and risk of immunogenicity, significant cost savings for treatment as well as reduced disruption to the patient and caregiver's lives.

As such, the present invention provides a method of treating a disease characterized by deposition of Aβ, comprising administering to a patient positive for amyloid deposits an induction dose of 10 to 60 mg/kg of an anti-N3pGlu Aβ antibody for a period of 6 month or less. Particularly, the present invention provides a method of treating a disease characterized by deposition of Aβ, comprising administering to a patient positive for amyloid deposits an induction dose of 10 to 60 mg/kg of an anti-N3pGlu Aβ antibody for a period of 6 month or less. More particularly, the present invention provides a method to treat a disease characterized by Aβ deposits in the brain of a human patient comprising administering to the patient positive for amyloid deposits a one-time induction dose of 10 to 60 mg/kg of an anti-N3pGlu antibody. In another more particular embodiment, the present invention provides a method to treat a disease characterized by Aβ deposits in the brain of a patient positive for amyloid deposits comprising administering to the patient an induction dose of 10 to 60 mg/kg every two weeks of an anti-N3pGlu Aβ antibody for a period of 6 months or less. In another more particular embodiment, the present invention provides a method to treat a disease characterized by Aβ deposits in the brain of a patient positive for amyloid deposits comprising administering to the patient a monthly induction dose of 10 to 60 mg/kg of an anti-N3pGlu Aβ antibody for a period of 6 months or less. In a preferred embodiment of the present invention, the one-time induction dose administered to a patient is 10 mg/kg, 15 mg/kg, 20 mg/kg or 40 mg-kg. In a alternative preferred embodiment of the present invention, the biweekly and monthly induction dose administered to a patient is 10 mg/kg, 15 mg/kg, 20 mg/kg or 40 mg/kg for a period of 6 months In another more preferred embodiment, the anti-N3pGlu Aβ antibody is selected from Table A.

Alternatively, the present invention provides a method of treating a disease characterized by deposition of Aβ, comprising administering to a patient positive for amyloid deposits a dose of 10 to 60 mg/kg of an anti-N3pGlu Aβ antibody followed optionally by one or more dose of 10 to 60 mg/kg of an anti-N3pGlu Aβ antibody for a period of 6 month or less. Particularly, the present invention provides a method to treat a disease characterized by Aβ deposits in the brain of a patient positive for amyloid deposits comprising administering to the patient 1-12 separate doses of 10 to 60 mg/kg of an anti-N3pGlu Aβ antibody in a period of 6 months or less. In another more particular embodiment, the present invention provides a method to treat a disease characterized by Aβ deposits in the brain of a patient positive for amyloid deposits comprising administering to the patient 6 separate doses of 10 to 60 mg/g of an anti-N3pGlu Aβ antibody for a period of 6 months or less. Alternatively, the present invention provides a method to treat a disease characterized by Aβ deposits in the brain of a patient positive for amyloid deposits comprising administering to the patient 12 separate doses of 10 to 60 mg/kg of an anti-N3pGlu Aβ antibody for a period of 6 months or less. In a preferred embodiment of the present invention, the 6 or 12 separate doses administered to a patient are 20 to 40 mg/g or 15 to 30 mg/g (e.g., 6 separate doses of 20 mg/kg administered to a patient over 6 months). In another preferred embodiment, the one-time, 6 or 12 separate doses administered to a patient is 10 mg/kg, 15 mg/kg, 20 mg/kg, or 40 mg/kg per dose. In another preferred embodiment the 6 separate doses are separated by monthly interval and the 12 separate doses are separated by intervals of 2 weeks. In a preferred embodiment, the anti-N3pGlu Aβ antibody is selected from Table A.

In an embodiment, the present invention provides a method of treating or preventing clinical or pre-clinical Alzheimer's disease, Down's syndrome, and clinical or pre-clinical CAA in a patient positive for amyloid deposits, comprising administering to a patient induction dose of 10 to 60 mg/kg of an anti-N3pGlu Aβ antibody for a period of 6 month or less. Particularly, the present invention provides a method of treating or preventing clinical or pre-clinical Alzheimer's disease, Down's syndrome, and clinical or pre-clinical CAA in a patient positive for amyloid deposits, comprising administering to the patient a one-time induction dose of 10 to 60 mg/kg of an anti-N3pGlu Aβ antibody. In another particular embodiment, the present invention provides a method of treating or preventing clinical or pre-clinical Alzheimer's disease, Down's syndrome, and clinical or pre-clinical CAA in a patient positive for amyloid deposits, administering to the an induction dose of 10 to 60 mg/kg every two weeks of an anti-N3pGlu Aβ antibody for a period of 6 months or less. In another particular embodiment, the present invention provides a method of treating or preventing clinical or pre-clinical Alzheimer's disease, Down's syndrome, and clinical or pre-clinical CAA in a patient positive for amyloid deposits, administering to the patient a monthly induction dose of 10 to 60 mg/kg of an anti-N3pGlu Aβ antibody for a period of 6 months or less. In a preferred embodiment of the invention for treating or preventing clinical or pre-clinical Alzheimer's disease, Down's syndrome, and clinical or pre-clinical CAA, the one-time, biweekly (every two weeks) and monthly induction dose administered to a patient is 20 to 40 mg kg or 15 to 30 mg kg. In a preferred embodiment of the present invention, the one-time induction dose administered to a patient is 10 mg/kg, 15 mg/kg, 20 mg/kg or 40 mg/kg. In a alternative preferred embodiment of the present invention, the biweekly and monthly induction dose administered to a patient is 10 mg/kg, 15 mg/kg, 20 mg/kg or 40 mg/kg for a period of 6 months In another more preferred embodiment, the anti-N3pGlu Aβ antibody is selected from Table A. The anti-N3pGlu Aβ antibody is preferably selected from Table A.

In another embodiment, the present invention provides a method of treating or preventing preclinical AD, prodromal AD (sometimes also referred to as AD-related mild cognitive impairment, MCI or MCI due to AD), mild AD, moderate AD and severe AD in a patient positive for amyloid deposits, comprising administering to a patient an induction dose of an anti-N3pGlu Aβ antibody for a period of 6 months or less. Particularly, the present invention provides a method of treating or preventing preclinical AD, prodromal AD, mild AD, moderate AD and severe AD in a patient positive for amyloid deposits, comprising administering to a patient an induction dose of 10 to 60 mg/kg of an anti-N3pGlu Aβ antibody for a period of 6 month or less. More particularly, the present invention provides a method of treating or preventing preclinical AD, prodromal AD, mild AD, moderate AD and severe AD in a patient positive for amyloid deposits, comprising administering to the patient a one-time induction dose of 10 to 60 mg/kg of an anti-N3pGlu Aβ antibody. In another more particular embodiment, the present invention provides a method of treating or preventing preclinical AD, prodromal AD, mild AD, moderate AD and severe AD in a patient positive for amyloid deposits, administering to the an induction dose of 10 to 60 mg/kg every two weeks of an anti-N3pGlu Aβ antibody for a period of 6 months or less. In another more particular embodiment, the present invention provides a method of treating or preventing preclinical AD, prodromal AD, mild AD, moderate AD and severe AD in a patient positive for amyloid deposits, administering to the patient a monthly induction dose of 10 to 60 mg/kg of an anti-N3pGlu Aβ antibody for a period of 6 months or less. In a preferred embodiment of the invention for treating or preventing preclinical AD, prodromal AD, mild AD, moderate AD and severe AD, the one-time, biweekly (every two weeks) and monthly induction dose administered to a patient is 20 to 40 mg/kg or 15 to 30 mg/kg. In a preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months In another more preferred embodiment, the anti-N3pGlu Aβ antibody is selected from Table A. The anti-N3pGlu Aβ antibody is preferably selected from Table A.

In another embodiment, the present invention provides a method of slowing cognitive decline in a patient diagnosed with pre-clinical Alzheimer's disease or clinical Alzheimer's disease, comprising administering to a patient an induction dose of an anti-N3pGlu Aβ antibody for a period of 6 months or less. Particularly, the present invention a method of slowing cognitive decline in a patient diagnosed with pre-clinical Alzheimer's disease or clinical Alzheimer's disease, comprising administering to a patient an induction dose of 10 to 60 mg/kg of an anti-N3pGlu Aβ antibody for a period of 6 month or less. More particularly, the present invention provides a method of slowing cognitive decline in a patient diagnosed with pre-clinical Alzheimer's disease or clinical Alzheimer's disease, comprising administering to the patient a one-time induction dose of 10 to 60 mg/kg of an anti-N3pGlu Aβ antibody. In another more particular embodiment, the present invention provides a method of slowing cognitive decline in a patient diagnosed with pre-clinical Alzheimer's disease or clinical Alzheimer's disease, administering to the patient an induction dose of 10 to 60 mg/kg every two weeks of an anti-N3pGlu Aβ antibody for a period of 6 months or less. In another more particular embodiment, the present invention provides a method of slowing cognitive decline in a patient diagnosed with pre-clinical Alzheimer's disease or clinical Alzheimer's disease, administering to the patient a monthly induction dose of 10 to 60 mg/kg of an anti-N3pGlu Aβ antibody for a period of 6 months or less. In a preferred embodiment of the invention for slowing cognitive decline in a patient diagnosed with pre-clinical Alzheimer's disease or clinical Alzheimer's disease, the one-time, biweekly and monthly induction dose administered to a patient is 20 to 40 mg/kg or 15 to 30 mg/kg. In a preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months In another more preferred embodiment, the anti-N3pGlu Aβ antibody is selected from Table A. The anti-N3pGlu Aβ antibody is preferably selected from Table A.

In another embodiment, the present invention provides a method of slowing functional decline in a patient diagnosed with pre-clinical Alzheimer's disease or clinical Alzheimer's disease, comprising administering to a patient an induction dose of an anti-N3pGlu Aβ antibody for a period of 6 months or less. Particularly, the present invention a method of slowing functional decline in a patient diagnosed with pre-clinical Alzheimer's disease or clinical Alzheimer's disease, comprising administering to a patient an induction dose of 10 to 60 mg/kg of an anti-N3pGlu Aβ antibody for a period of 6 month or less. More particularly, the present invention provides a method of slowing functional decline in a patient diagnosed with pre-clinical Alzheimer's disease or clinical Alzheimer's disease, comprising administering to the patient a one-time induction dose of 10 to 60 mg/kg of an anti-N3pGlu Aβ antibody. In another more particular embodiment, the present invention provides a method of slowing functional decline in a patient diagnosed with pre-clinical Alzheimer's disease or clinical Alzheimer's disease, administering to the patient an induction dose of 10 to 60 mg/kg every two weeks of an anti-N3pGlu Aβ antibody for a period of 6 months or less. In another more particular embodiment, the present invention provides a method of slowing functional decline in a patient diagnosed with pre-clinical Alzheimer's disease or clinical Alzheimer's disease, administering to the patient a monthly induction dose of 10 to 60 mg/kg of an anti-N3pGlu Aβ antibody for a period of 6 months or less. In a preferred embodiment of the invention for slowing functional decline in a patient diagnosed with pre-clinical Alzheimer's disease or clinical Alzheimer's disease, the one-time, biweekly and monthly induction dose administered to a patient is 20 to 40 mg/kg or 15 to 30 mg/kg. In a preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. The anti-N3pGlu Aβ antibody is preferably selected from Table A.

In another embodiment the present invention provides a method of reducing brain AB amyloid plaque load in a patient diagnosed with pre-clinical or clinical Alzheimer's disease, comprising administering to a patient an induction dose of an anti-N3pGlu Aβ antibody for a period of 6 months or less. Particularly, the present invention provides a method of reducing brain AD amyloid plaque load in a patient diagnosed with pre-clinical or clinical Alzheimer's disease, comprising administering to a patient an induction dose of 10 to 60 mg/kg of an anti-N3pGlu Aβ antibody for a period of 6 month or less. More particularly, the present invention provides a method of reducing brain Aβ amyloid plaque load in a patient diagnosed with pre-clinical or clinical Alzheimer's disease, comprising administering to the patient a one-time induction dose of 10 to 60 mg/kg of an anti-N3pGlu Aβ antibody. In another more particular embodiment, the present invention provides a method of reducing brain Aβ amyloid plaque load in a patient diagnosed with pre-clinical or clinical Alzheimer's disease, administering to the patient an induction dose of 10 to 60 mg/kg every two weeks of an anti-N3pGlu Aβ antibody for a period of 6 months or less. In another more particular embodiment, the present invention provides a method of reducing brain Aβ amyloid plaque load in a patient diagnosed with pre-clinical or clinical Alzheimer's disease, administering to the patient a monthly induction dose of 10 to 60 mg/kg of an anti-N3pGlu Aβ antibody for a period of 6 months or less. In a preferred embodiment of the invention for a method of reducing brain Aβ amyloid plaque load in a patient diagnosed with pre-clinical or clinical Alzheimer's disease, the one-time, biweekly and monthly induction dose administered to a patient is 20 to 40 mg/kg or 15 to 30 mg/kg. In a preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. The anti-N3pGlu Aβ antibody is preferably selected from Table A.

In another embodiment the present invention provides a method of preventing memory loss or cognitive decline in clinically asymptomatic patients with low levels of Aβ1-42 in the cerebrospinal fluid (CSF) and/or Aβ deposits in the brain, comprising administering to a patient an induction dose of an anti-N3pGlu Aβ antibody for a period of 6 months or less. Particularly, the present invention provides a method of preventing memory loss or cognitive decline in clinically asymptomatic patients with low levels of Aβ1-42 in the cerebrospinal fluid (CSF) and/or Aβ deposits in the brain, comprising administering to a patient an induction dose of 10 to 60 mg/kg of an anti-N3pGlu Aβ antibody for a period of 6 month or less. More particularly, the invention provides a method of preventing memory loss or cognitive decline in clinically asymptomatic patients with low levels of Aβ1-42 in the cerebrospinal fluid (CSF) and/or AD deposits in the brain, comprising administering to the patient a one-time induction dose of 10 to 60 mg/kg of an anti-N3pGlu Aβ antibody. In another more particular embodiment, the present invention provides a method of preventing memory loss or cognitive decline in clinically asymptomatic patients with low levels of Aβ 142 in the cerebrospinal fluid (CSF) and/or Aβ deposits in the brain, comprising administering to the patient an induction dose of 10 to 60 mg/kg every two weeks of an anti-N3pGlu Aβ antibody for a period of 6 months or less. In another more particular embodiment, the present invention provides a method of preventing memory loss or cognitive decline in clinically asymptomatic patients with low levels of Aβ1-42 in the cerebrospinal fluid (CSF) and/or Aβ deposits in the brain, administering to the patient a monthly induction dose of 10 to 60 mg/kg of an anti-N3pGlu Aβ antibody for a period of 6 months or less. In a preferred embodiment of the invention for a method of preventing memory loss or cognitive decline in clinically asymptomatic patients with low levels of Aβ1-42 in the cerebrospinal fluid (CSF) and/or Aβ deposits in the brain, the one-time, biweekly and monthly induction dose administered to a patient is 20 to 40 mg/kg or 15 to 30 mg/kg. In another preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. The anti-N3pGlu Aβ antibody is preferably selected from Table A.

In another embodiment the present invention provides a method of treating clinically asymptomatic patients known to have an Alzheimer's disease-causing genetic mutation, comprising administering to a patient an induction dose of an anti-N3pGlu Aβ antibody for a period of 6 months or less. Particularly, the present provides a method of treating clinically asymptomatic patients known to have an Alzheimer's disease-causing genetic mutation, comprising administering to a patient an induction dose of 10 to 60 mg/kg of an anti-N3pGlu Aβ antibody for a period of 6 month or less. More particularly, the invention provides a method of treating clinically asymptomatic patients known to have an Alzheimer's disease-causing genetic mutation, comprising administering to the patient a one-time induction dose of 10 to 60 mg/kg of an anti-N3pGlu Aβ antibody. In another more particular embodiment, the present invention provides a method of treating clinically asymptomatic patients known to have an Alzheimer's disease-causing genetic mutation, comprising administering to the patient an induction dose of 10 to 60 mg/kg every two weeks of an anti-N3pGlu Aβ antibody for a period of 6 months or less. In another more particular embodiment, the present invention provides a method of treating clinically asymptomatic patients known to have an Alzheimer's disease-causing genetic mutation, administering to the patient a monthly induction dose of 10 to 60 mg/kg of an anti-N3pGlu Aβ antibody for a period of 6 months or less. In the present invention "clinically asymptomatic patients known to have an Alzheimer's disease-causing genetic mutation", include patients known to have a PSEN1 E280A Alzheimer's disease-causing genetic mutation (Paisa mutation), a genetic mutation that causes autosomal-dominant Alzheimer's disease or are at higher risk for developing AD by virtue of carrying one or two APOE e4 alleles comprising administering to the said patient a pharmaceutical composition of the present invention. In a preferred embodiment of the invention for a method of treating clinically asymptomatic patients known to have an Alzheimer's disease-causing genetic mutation, the one-time, biweekly and monthly induction dose administered to a patient is 20 to 40 mg/kg or 15 to 30 mg/kg. In another preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. The anti-N3pGlu Aβ antibody is preferably selected from Table A.

In a further embodiment, the present invention provides a method of treating a disease characterized by deposition of Aβ in the brain, comprising administering to a patient an induction dose of an anti-N3pGlu Aβ antibody for a period of 6 months or less, wherein the Aβ deposit in the brain of a human patient is reduced by 35-100% within 6 months post induction dose treatment. Particularly, the present invention provides a method of treating a disease characterized by deposition of Aβ, comprising administering to a patient an induction dose of 10 to 60 mg kg of an anti-N3pGlu Aβ antibody for a period of 6 month or less, wherein the Aβ deposit in the brain of a human patient is reduced by 35-100% within 6 months post induction dose treatment. More particularly, the present invention provides a method to treat a disease characterized by Aβ deposits in the brain of a human patient comprising administering to the patient a one-time induction dose of 10 to 60 mg/kg of an anti-N3pGlu Aβ antibody, wherein the Aβ deposit in the brain of a human patient is reduced by 35-100% within 6 months post induction dose treatment. In another more particular embodiment, the present invention provides a method to treat a disease characterized by Aβ deposits in the brain of a patient comprising administering to the patient an induction dose of 10 to 60 mg/kg every two weeks of an anti-N3pGlu Aβ antibody for a period of 6 months or less, wherein the Aβ deposit in the brain of a human patient is reduced by 35-100% within 6 months post induction dose treatment. In another more particular embodiment, the present invention provides a method to treat a disease characterized by Aβ deposits in the brain of a patient comprising administering to the patient a monthly induction dose of 10 to 60 mg/kg of an anti-N3pGlu Aβ antibody for a period of 6 months or less, wherein the Aβ deposit in the brain of a human patient is reduced by 35-100% within 6 months post induction dose treatment. In a preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. The anti-N3pGlu Aβ antibody is preferably selected from Table A.

In an embodiment, the present invention provides a method of treating clinical or pre-clinical Alzheimer's disease, Down's syndrome, and clinical or pre-clinical cerebral amyloid angiopathy, comprising administering to a patient an induction dose of an anti-N3pGlu Aβ antibody for a period of 6 months or less, wherein the Aβ deposit in the brain of a human patient is reduced by 35-100% within 6 months post induction dose treatment. Particularly, the present invention a method of treating clinical or pre-clinical Alzheimer's disease, Down's syndrome, and clinical or pre-clinical cerebral amyloid angiopathy, comprising administering to a patient an induction dose of 10 to 60 mg/kg of an anti-N3pGlu Aβ antibody for a period of 6 month or less, wherein the Aβ deposit in the brain of a human patient is reduced by 35-100% within 6 months post induction treatment. More particularly, the present invention provides a method of treating clinical or pre-clinical Alzheimer's disease. Down's syndrome, and clinical or pre-clinical cerebral amyloid angiopathy, comprising administering to the patient a one-time induction dose of 10 to 60 mg/kg of an anti-N3pGlu Aβ antibody, wherein the Aβ deposit in the brain of a human patient is reduced by 35-100% within 6 months post induction treatment. In another more particular embodiment, the present invention provides a method of treating clinical or pre-clinical Alzheimer's disease, Down's syndrome, and clinical or pre-clinical cerebral amyloid angiopathy, comprising administering to the patient an induction dose of 10 to 60 mg/kg every two weeks of an anti-N3pGlu Aβ antibody for a period of 6 months or less, wherein the Aβ deposit in the brain of a human patient is reduced by 35-100% within 6 months post induction treatment. In another more particular embodiment, the present invention provides a method of treating clinical or pre-clinical Alzheimer's disease. Down's syndrome, and clinical or pre-clinical cerebral amyloid angiopathy, comprising administering to the patient a monthly induction dose of 10 to 60 mg/kg of an anti-N3pGlu Aβ antibody for a period of 6 months or less, wherein the Aβ deposit in the brain of a human patient is reduced by 35-100% within 6 months post induction treatment. In an embodiment of the preferred invention, the anti-N3pGlu Aβ antibody is selected from Table A.

In an embodiment, the present invention provides a method of slowing cognitive and/or functional decline in a patient diagnosed with pre-clinical Alzheimer's disease or clinical Alzheimer's disease, comprising administering to a patient an induction dose of an anti-N3pGlu Aβ antibody for a period of 6 months or less, wherein the Aβ deposit in the brain of a human patient is reduced by 35-100% within 6 months post induction dose treatment. Particularly, the present invention a method of slowing cognitive and/or functional decline in a patient diagnosed with pre-clinical Alzheimer's disease or clinical Alzheimer's disease, comprising administering to a patient an induction dose of 10 to 60 mg/kg of an anti-N3pGlu Aβ antibody for a period of 6 month or less, wherein the Aβ deposit in the brain of a human patient is reduced by 35-100% within 6 months post induction treatment. More particularly, the present invention provides a method of slowing cognitive and/or functional decline in a patient diagnosed with pre-clinical Alzheimer's disease or clinical Alzheimer's disease, comprising administering to the patient a one-time induction dose of 10 to 60 mg/kg of an anti-N3pGlu Aβ antibody, wherein the AD deposit in the brain of a human patient is reduced by 35-100% within 6 months post induction treatment. In another more particular embodiment, the present invention provides slowing cognitive and/or functional decline in a patient diagnosed with pre-clinical Alzheimer's disease or clinical Alzheimer's disease, comprising administering to the patient an induction dose of 10 to 60 mg/kg every two weeks of an anti-N3pGlu Aβ antibody for a period of 6 months or less, wherein the Aβ deposit in the brain of a human patient is reduced by 35-100% within 6 months post induction treatment. In another more particular embodiment, the present invention provides a method of slowing cognitive and/or functional decline in a patient diagnosed with pre-clinical Alzheimer's disease or clinical Alzheimer's disease, comprising administering to the patient a monthly induction dose of 10 to 60 mg/kg of an anti-N3pGlu Aβ antibody for a period of 6 months or less, wherein the Aβ deposit in the brain of a human patient is reduced by 35-100% within 6 months post induction treatment. In a preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg kg, 20 mg/kg or 40 ng/kg for a period of 6 months. The anti-N3pGlu Aβ antibody is preferably selected from Table A In an embodiment, the present invention provides a method of treating clinical or pre-clinical Alzheimer's disease. Down's syndrome, and clinical or pre-clinical CAA with an anti-N3pGlu Aβ antibody for a period of 6 months or less, wherein the Aβ deposit in the brain of a human patient is reduced by 35-100% within 6 months post induction treatment and maintained in a reduced state for a period of 2-10 years post treatment. More preferably, for 2-5 years. Even more preferably, for 5-10 years. Particularly, the present invention provides a method of treating clinical or pre-clinical Alzheimer's disease, Down's syndrome, and clinical or pre-clinical cerebreal amyloid angiopathy, comprising administering to a patient an induction dose of 10 to 60 mg/kg of an anti-N3pGlu Aβ antibody for a period of 6 month or less, wherein the Aβ deposit in the brain of a human patient is reduced by 35-100% within 6 months post induction treatment and maintained in a reduced state for a period of 2-10 years post treatment. More preferably, for 2-5 years. Even more preferably, for 5-10 years. More particularly, the present invention provides a method of treating clinical or pre-clinical Alzheimer's disease, Down's syndrome, and clinical or pre-clinical cerebral amyloid angiopathy, comprising administering to the patient a one-time induction dose of 10 to 60 mg/kg of an anti-N3pGlu Aβ antibody, wherein the Aβ deposit in the brain of a human patient is reduced by 35-100% within 6 months post induction treatment and maintained in a reduced state for a period of 1-10 years post treatment. More preferably, for 2-5 years. Even more preferably, for 5-10 years. In another more particular embodiment, the present invention provides a method of treating clinical or pre-clinical Alzheimer's disease, Down's syndrome, and clinical or pre-clinical cerebral amyloid angiopathy, comprising administering to the patient an induction dose of 10 to 60 mg/kg every two weeks of an anti-N3pGlu Aβ antibody for a period of 6 months or less, wherein the Aβ deposit in the brain of a human patient is reduced by 35-100% within 6 months post induction treatment and maintained in a reduced state for a period of 2-10 years post treatment. More preferably, for 2-5 years. Even more preferably, for 5-10 years. In another more particular embodiment, the present invention provides a method of treating clinical or pre-clinical Alzheimer's disease. Down's syndrome, and clinical or pre-clinical cerebral amyloid angiopathy, comprising administering to the patient a monthly induction dose of 10 to 60 mg/kg of an anti-N3pGlu Aβ antibody for a period of 6 months or less, wherein the AD deposit in the brain of a human patient is reduced by 35-100% within 6 months post induction treatment and maintained in a reduced state for a period of 2-10 years post treatment. More preferably, for 2-5 years. Even more preferably, for 5-10 years. In a preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. The anti-N3pGlu Aβ antibody is preferably selected from Table A.

The present invention also provides a method of treating a disease characterized by deposition of Aβ in the brain, comprising administering to a patient an induction dose of an anti-N3pGlu Aβ antibody for a period of 6 months or less followed by a maintenance dose of an anti-N3pGlu Aβ antibody every 12, 3, 5 or 10 years post completion of the induction treatment. Particularly, the present invention provides a method to treat a disease characterized by Aβ deposits in the brain of a human patient comprising administering to the patient positive for amyloid deposits a one-time induction dose of 10 to 60 mg/kg of an anti-N3pGlu Aβ antibody followed by a maintenance dose of an anti-N3pGlu Aβ antibody every 1, 2, 3, 5 or 10 years post completion of the induction treatment. In another more particular embodiment, the present invention provides a method to treat a disease characterized by All deposits in the brain of a patient positive for amyloid deposits comprising administering to the patient an induction dose of 10 to 60 mg/kg every two weeks of an anti-N3pGlu Aβ antibody for a period of 6 months or less followed by a maintenance dose of an anti-N3pGlu Aβ antibody every 1, 2, 3, 5 or 10 years post completion of the induction treatment. In another more particular embodiment, the present invention provides a method to treat a disease characterized by Aβ deposits in the brain of a patient positive for amyloid deposits comprising administering to the patient a monthly induction dose of 10 to 60 mg/kg of an anti-N3pGlu Aβ antibody for a period of 6 months or less followed by a maintenance dose of an anti-N3pGlu Aβ antibody every 1, 2, 3, 5 or 10 years post completion of the induction treatment. In one particular embodiment the maintenance dose of an Aβ antibody is given every year. In another particular embodiment the maintenance dose of an Aβ antibody is given every 2 years. In another particular embodiment the maintenance dose of an Aβ antibody is given every 3 years. In another particular embodiment the maintenance dose of an Aβ antibody is given every 5 years. In another particular embodiment the maintenance dose of an Aβ antibody is given every 10 years. In another particular embodiment the maintenance dose of an Aβ antibody is given every 2 to 5 years. In another particular embodiment the maintenance dose of an Aβ antibody is given every 5 to 10 years. In an embodiment of the present invention the same anti-N3pGlu Aβ antibody is used for the induction and maintenance dose. In another embodiment of the present invention different anti-N3pGlu antibodies are used for the induction and maintenance doses. In an embodiment of the more particular invention, the anti-N3pGlu Aβ antibody administered in the induction and maintenance dose is selected from Table A.

In an embodiment, the present invention also provides a method of treating a disease characterized by deposition of Aβ in the brain, comprising administering to a patient an induction dose of an anti-N3pGlu Aβ antibody for a period of 6 months or less in simultaneous, separate, or sequential combination with an effective amount of a BACE inhibitor. In a particular embodiment, the present invention provides a method of treating a disease characterized by deposition of Aβ in the brain comprising administering to the patient a one-time induction dose of 10 to 60 mg/kg of an anti-N3pGlu Aβ antibody in simultaneous, separate, or sequential combination with an effective amount of a BACE inhibitor. In another particular embodiment, the present invention provides a method of treating a disease characterized by deposition of AD in the brain comprising administering to the patient an induction dose of 10 to 60 mg/kg every two weeks of an anti-N3pGlu Aβ antibody for a period of 6 months or less in simultaneous, separate, or sequential combination with an effective amount of a BACE inhibitor. In another particular embodiment, the present invention provides a method of treating a disease characterized by deposition of Aβ in the brain, comprising administering to the patient a monthly induction dose of 10 to 60 mg/kg of an anti-N3pGlu Aβ antibody for a period of 6 months or less in simultaneous, separate, or sequential combination with an effective amount of a BACE inhibitor. In another preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months.

In a more particular embodiment of the present invention, the anti-N3pGlu Aβ antibody is preferably selected from Table A and the BACE inhibitor is selected from the group consisting of a) a compound of formula

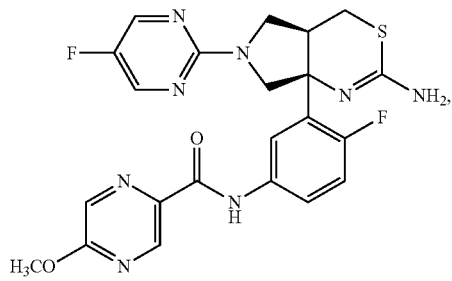 [SMILES: COc1cnc(C(=O)Nc2ccc(F)c([C@]34CN(c5ncc(F)cn5)C[C@H]3CSC(N)=N4)c2)cn1]

also referred to by the compound name N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide, or a pharmaceutically acceptable salt thereof;
b) tosylate salt of N-[3-[(4aR,7aS)-2-amino-6-(5-fluoro-pyrimidin-2-yl)-4,4a,5,7-tetrahydropyrrolo[3,4-d][1,3]thiazin-7a-yl]-4-fluoro-phenyl]-5-methoxy-pyrazine-2-carboxamide;
c) crystalline form of 2 N-[3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl]-5-methoxy-pyrazine-2-carboxamide; and d) a compound of the formula

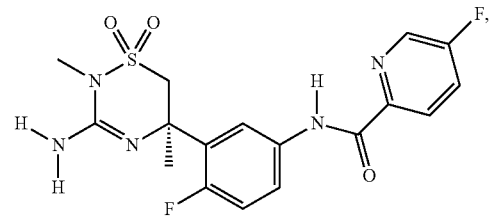 [SMILES: CN1C(N)=N[C@](C)(c2cc(NC(=O)c3ccc(F)cn3)ccc2F)CS1(=O)=O]

also referred to by the compound name N-[3-[(5R)-3-Amino-5,6-dihydro-2,5-dimethyl-1,1-dioxido-2H-1,2,4-thiadiazin-5-yl]-4-fluorophenyl]-5-fluoro-2-pyridinecarboxamide or the generic name, verubecestat, or a pharmaceutically acceptable salt thereof.

In another more particular embodiment of the present invention, the anti-N3pGlu Aβ antibody is preferably B12L and the BACE inhibitor is selected from the group consisting of a) a compound of formula

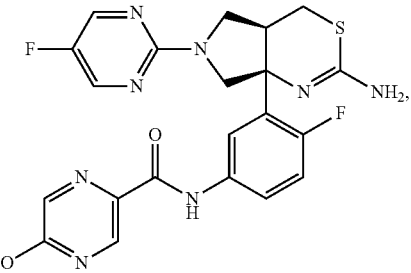

also referred to by the compound name N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide, or a pharmaceutically acceptable salt thereof;
b) tosylate salt of N-[3-[(4aR,7aS)-2-amino-6-(5-fluoro-pyrimidin-2-yl)-4,4a,5,7-tetrahydropyrrolo[3,4-d][1,3]thiazin-7a-yl]-4-fluoro-phenyl]-5-methoxy-pyrazine-2-carboxamide;
c) crystalline form of 2 N-[3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl]-5-methoxy-pyrazine-2-carboxamide; and
d) a compound of the formula

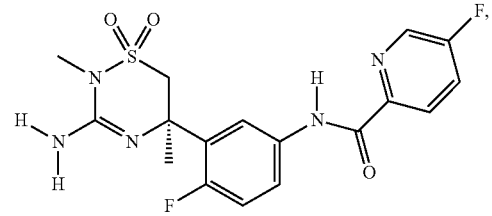 [SMILES: CN1C(N)=N[C@](C)(c2cc(NC(=O)c3ccc(F)cn3)ccc2F)CS1(=O)=O]

also referred to by the compound name N-[3-[(5R)-3-Amino-5,6-dihydro-2,5-dimethyl-1,1-dioxido-2H-1,2,4-thiadiazin-5-yl]-4-fluorophenyl]-5-fluoro-2-pyridinecarboxamide or the generic name, verubecestat, or a pharmaceutically acceptable salt thereof.

In an embodiment, the present invention also provides a method of treating a disease characterized by deposition of Aβ in the brain, comprising administering to a patient a one-time induction dose of an anti-N3pGlu Aβ antibody for a period of 6 months or less in simultaneous, separate, or sequential combination with an effective amount of an Aβ antibody. In a particular embodiment, the present invention also provides a method of treating a disease characterized by deposition of Aβ in the brain, comprising administering to a patient a one-time, biweekly or monthly induction dose of 10 to 60 mg/kg of an anti-N3pGlu Aβ antibody for a period of 6 months or less in simultaneous, separate, or sequential combination with an effective amount of an Aβ antibody, wherein the Aβ antibody comprises an amino acid light chain (LC) and an amino acid heavy chain (HC) selected from the group consisting of;

A) LC of SEQ ID NO: 65 and HC of SEQ ID NO:66 (solanezumab);
B) LC of SEQ ID NO: 61 and HC of SEQ ID NO: 62 (crenezumab):
C) LC of SEQ ID NO: 57 and HC of SEQ ID NO: 58 (aducunumab):
D) LC of SEQ ID NO: 63 and HC of SEQ ID NO: 64 (BAN2401) and;
E) LC of SEQ ID NO: 59 and HC of SEQ ID NO: 60 (gantenerunmab).

In a preferred embodiment of the present invention, the one-time biweekly and monthly induction dose administered to a patient is 10 mg/kg, 15 mg/kg, 20 mg/kg or 40 mg/kg. The anti-N3pGlu Aβ antibody is preferably selected from Table A.

In an embodiment, the present invention also provides a method of treating a disease characterized by deposition of Aβ in the brain, comprising administering to a patient a one-time, biweekly or monthly induction dose of 10 to 60 mg/kg of an anti-N3pGlu Aβ antibody for a period of 6 months or less in simultaneous, separate, or sequential combination with an effective amount of a 20 kD pegylated anti-AD Fab antibody, wherein the anti-AD Fab comprises an amino acid light chain variable region of SEQ ID NO: 55 and an amino acid heavy chain variable region of SEQ ID NO:56. In a preferred embodiment of the present invention, the one-time biweekly and monthly induction dose administered to a patient is 10 mg/kg, 15 mg/kg, 20 mg/kg or 40 mg/kg. The anti-N3pGlu Aβ antibody is preferably selected from Table A.

In another embodiment of the present invention also provides a method of treating a disease characterized by deposition of Aβ in the brain, comprising administering to a patient a one-time, biweekly or monthly induction dose of 10 to 60 mg/kg of an anti-N3pGlu Aβ antibody for a period of 6 months or less in simultaneous, separate, or sequential combination with an effective amount of a symptomatic agent to treat Alzheimer's disease. Symptomatic agents can be selected from cholinesterase inhibitors (ChEIs) and/or a partial N-methyl-D-aspartate (NMDA) antagonists. In a preferred embodiment the agent is a ChEI. In another preferred embodiment the agent is a NMDA antagonist or a combination agent comprising a ChEI and NMDA antagonist. In a more preferred embodiment of the present invention, the one-time induction dose administered to a patient is 10 mg/kg, 15 mg/kg, 20 mg/kg or 40 mg/kg. In an alternative more preferred embodiment of the present invention, the biweekly and monthly induction dose administered to a patient is 10 mg/kg, 15 mg/kg, 20 mg/kg or 40 mg/kg for a period of 6 months. The anti-N3pGlu Aβ antibody is preferably selected from Table A.

In another embodiment the present invention provides an anti-N3pGlu Aβ antibody for use in the treatment of clinical or pre-clinical Alzheimer's disease, Down's syndrome, and clinical or pre-clinical cerebral amyloid angiopathy, wherein the anti-N3pGlu Aβ antibody is administered to a patient at a dose of 10 to 60 mg/kg for a period of 6 months or less. Particularly, the present invention provides an anti-N3pGlu Aβ antibody for use in treatment of clinical or pre-clinical Alzheimer's disease. Down's syndrome, and clinical or pre-clinical cerebral amyloid angiopathy, wherein the anti-N3pGlu Aβ antibody is administered to a patient as a one-time induction dose of 10 to 60 mg/kg of an anti-N3pGlu Aβ antibody. In another more particular embodiment, the present invention provides an anti-N3pGlu Aβ antibody for use in the treatment of clinical or pre-clinical Alzheimer's disease, Down's syndrome, and clinical or pre-clinical cerebral amyloid angiopathy, wherein the anti-N3pGlu Aβ antibody is administered to a patient as an induction dose of 10 to 60 mg/kg every two weeks of an anti-N3pGlu Aβ antibody for a period of 6 months or less. In another more particular embodiment, the present invention an anti-N3pGlu Aβ antibody for use in the treatment of clinical or pre-clinical Alzheimer's disease, Down's syndrome, and clinical or pre-clinical cerebral amyloid angiopathy, wherein the anti-N3pGlu Aβ antibody is administered to a patient as an induction dose of 10 to 60 mg/kg monthly for a period of 6 months or less. In a preferred embodiment of the invention for use in the treatment or preventing of clinical or pre-clinical Alzheimer's disease, Down's syndrome, and clinical or pre-clinical CAA, the one-time, biweekly and monthly induction dose administered to a patient is 20 to 40 mg/kg or 15 to 30 mg/kg. In a preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. Even more preferably, the anti-N3pGlu Aβ antibody is selected from Table A.

In another embodiment the present invention provides an anti-N3pGlu Aβ antibody for use in the treatment of prodromal AD, mild AD, moderate AD or severe AD, wherein the anti-N3pGlu Aβ antibody is administered to a patient at a dose of 10 to 60 mg/kg for a period of 6 months or less. Particularly, the present invention provides an anti-N3pGlu Aβ antibody for use in the treatment of prodromal AD, mild AD, moderate AD or severe AD, wherein the anti-N3pGlu Aβ antibody is administered to a patient as a one-time induction dose of 10 to 60 mg/kg of an anti-N3pGlu Aβ antibody. In another more particular embodiment, the present invention provides an anti-N3pGlu Aβ antibody for use in the treatment of prodromal AD, mild AD, moderate AD or severe AD, wherein the anti-N3pGlu Aβ antibody is administered to a patient as an induction dose of 10 to 60 mg/kg every two weeks of an anti-N3pGlu Aβ antibody for a period of 6 months or less. In another more particular embodiment, the present invention an anti-N3pGlu Aβ antibody for use in the treatment of prodromal AD, mild AD, moderate AD or severe AD, wherein the anti-N3pGlu Aβ antibody is administered to a patient as an induction dose of 10 to 60 mg/kg monthly for a period of 6 months or less. In a preferred embodiment for use in the in the treatment of prodromal AD, mild AD, moderate AD or severe AD, the one-time, biweekly and monthly induction dose administered to a patient is 20 to 40 mg/kg or 15 to 30 mg/kg. In a preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. Even more preferably, the anti-N3pGlu Aβ antibody is selected from Table A.

In another embodiment the present invention provides an anti-N3pGlu Aβ antibody for use in preventing or slowing cognitive or functional decline in a patient diagnosed with a condition selected from clinical or pre-clinical Alzheimer's disease, Down's syndrome, and clinical or pre-clinical cerebral amyloid angiopathy, wherein the anti-N3pGlu Aβ antibody is administered to a patient at a dose of 10 to 60 mg/kg for a period of 6 months or less. Particularly, the present invention provides an anti-N3pGlu Aβ antibody for use in preventing or slowing cognitive decline in a patient diagnosed with a condition selected from clinical or pre-clinical Alzheimer's disease, Down's syndrome, and clinical or pre-clinical cerebral amyloid angiopathy, wherein the anti-N3pGlu Aβ antibody is administered to a patient as a one-time induction dose of 10 to 60 mg/kg of an anti-N3pGlu Aβ antibody. In another more particular embodiment, the present invention provides an anti-N3pGlu Aβ antibody for use in preventing or slowing cognitive decline in a patient diagnosed with a condition selected from clinical or pre-clinical Alzheimer's disease, Down's syndrome, and clinical or pre-clinical cerebral amyloid angiopathy, moderate AD or severe AD, wherein the anti-N3pGlu Aβ antibody is administered to a patient as an induction dose of 10 to 60 mg/kg every two weeks of an anti-N3pGlu Aβ antibody for a period of 6 months or less. In another more particular embodiment, the present invention an anti-N3pGlu Aβ antibody for use in preventing or slowing cognitive decline in a patient diagnosed with a condition selected from clinical or pre-clinical Alzheimer's disease, Down's syndrome, and clinical or pre-clinical cerebral amyloid angiopathy, wherein the anti-N3pGlu Aβ antibody is administered to a patient as an induction dose of 10 to 60 mg/kg monthly for a period of 6 months or less. In a preferred embodiment of the invention for use in preventing or slowing cognitive decline in a patient diagnosed with a condition selected from clinical or pre-clinical Alzheimer's disease, Down's syndrome, and clinical or pre-clinical cerebral amyloid angiopathy, the one-time, biweekly and monthly induction dose administered to a patient is 20 to 40 mg/kg or 15 to 30 mg/kg. In a preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. Even more preferably, the anti-N3pGlu Aβ antibody is selected from Table A.

In another embodiment the present invention provides an anti-N3pGlu Aβ antibody for use in reducing Aβ amyloid plaque load in the brain of a patient diagnosed with pre-clinical or clinical Alzheimer's disease, Down's syndrome, and clinical or pre-clinical cerebral amyloid angiopathy, wherein the anti-N3pGlu Aβ antibody is administered to a patient at a dose of 10 to 60 mg/kg for a period of 6 months or less. Particularly, the present invention provides an anti-N3pGlu Aβ antibody for use in reducing Aβ amyloid plaque load in the brain of a patient diagnosed with pre-clinical or clinical Alzheimer's disease, Down's syndrome, and clinical or pre-clinical cerebral amyloid angiopathy, wherein the anti-N3pGlu Aβ antibody is administered to a patient as a one-time induction dose of 10 to 60 mg/kg of an anti-N3pGlu Aβ antibody. In another more particular embodiment, the present invention provides an anti-N3pGlu Aβ antibody for use in reducing Aβ amyloid plaque load in the brain of a patient diagnosed with pre-clinical or clinical Alzheimer's disease, Down's syndrome, and clinical or pre-clinical cerebral amyloid angiopathy, wherein the anti-N3pGlu Aβ antibody is administered to a patient as an induction dose of 10 to 60 mg/kg every two weeks of an anti-N3pGlu Aβ antibody for a period of 6 months or less. In another more particular embodiment, the present invention provides an anti-N3pGlu Aβ antibody for use in reducing Aβ amyloid plaque load in the brain of a patient diagnosed with pre-clinical or clinical Alzheimer's disease, Down's syndrome, and clinical or pre-clinical cerebral amyloid angiopathy, wherein the anti-N3pGlu Aβ antibody is administered to a patient as an induction dose of 10 to 60 mg/kg monthly for a period of 6 months or less. In a preferred embodiment of the invention for use in reducing Aβ amyloid plaque load in the brain of a patient diagnosed with pre-clinical or clinical Alzheimer's disease, Down's syndrome, and clinical or pre-clinical cerebral amyloid angiopathy, the one-time, biweekly and monthly induction dose administered to a patient is 20 to 40 mg/kg or 15 to 30 mg/kg. In another preferred embodiment of the present invention, the one-time induction dose administered to a patient is 10 mg/kg, 15 mg-kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. Even more preferably, the anti-N3pGlu Aβ antibody is selected from Table A.

In another embodiment the present invention provides an anti-N3pGlu Aβ antibody for use in treating clinically asymptomatic patients known to have Alzheimer's disease causing genetic mutation, wherein the anti-N3pGlu Aβ antibody is administered to a patient at a dose of 10 to 60 mg/kg for a period of 6 months or less. Particularly, the present invention provides an anti-N3pGlu Aβ antibody for use in treating asymptomatic patients known to have Alzheimer's disease causing genetic mutation, wherein the anti-N3pGlu Aβ antibody is administered to a patient as a one-time induction dose of 10 to 60 mg/kg of an anti-N3pGlu Aβ antibody. In another more particular embodiment, the present invention provides an anti-N3pGlu Aβ antibody for use in treating asymptomatic patients known to have Alzheimer's disease causing genetic mutation, wherein the anti-N3pGlu Aβ antibody is administered to a patient as an induction dose of 10 to 60 mg/kg every two weeks of an anti-N3pGlu Aβ antibody for a period of 6 months or less. In another more particular embodiment, the present invention provides an anti-N3pGlu Aβ antibody for use in treating asymptomatic patients known to have Alzheimer's disease causing genetic mutation, wherein the anti-N3pGlu Aβ antibody is administered to a patient as an induction dose of 10 to 60 mg/kg monthly for a period of 6 months or less. In a preferred embodiment of the invention for use in treating asymptomatic patients known to have Alzheimer's disease causing genetic mutation, the one-time, biweekly and monthly induction dose administered to a patient is 20 to 40 mg/kg or 15 to 30 mg/kg. In a preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. The anti-N3pGlu Aβ antibody is selected from Table A.

In another embodiment the present invention provides for a use of an anti-N3pGlu Aβ antibody for the manufacture of a medicament for the treatment of clinical or pre-clinical Alzheimer's disease, Down's syndrome, and clinical or pre-clinical cerebral amyloid angiopathy, wherein the medicament comprises an induction dose of 10 to 60 mg/kg of an anti-N3pGlu Aβ antibody administered to a patient for a period of 6 months or less. Particularly, the present invention provides for a use of an anti-N3pGlu Aβ antibody for the manufacture of a medicament for the treatment of clinical or pre-clinical Alzheimer's disease, Down's syndrome, and clinical or pre-clinical cerebral amyloid angiopathy, wherein the medicament comprises a one-time induction dose of 10 to 60 mg/kg of an anti-N3pGlu Aβ antibody administered to a patient. In another more particular embodiment, the present invention provides for a use of an anti-N3pGlu Aβ antibody for the manufacture of a medicament for the treatment of clinical or pre-clinical Alzheimer's disease, Down's syndrome, and clinical or pre-clinical cerebral amyloid angiopathy, wherein the medicament comprises an induction dose of 10 to 60 mg/kg of an anti-N3pGlu Aβ antibody administered to a patient every two weeks for a period of 6 months or less. In another more particular embodiment, the present invention provides for a use of an anti-N3pGlu Aβ antibody for the manufacture of a medicament for the treatment of clinical or pre-clinical Alzheimer's disease, Down's syndrome, and clinical or pre-clinical cerebral amyloid angiopathy, wherein the medicament comprises an induction dose of 10 to 60 mg/kg of an anti-N3pGlu Aβ antibody administered to a patient every month for a period of 6 months or less. In a preferred embodiment of the invention the one-time, biweekly and monthly induction dose administered to a patient is 20 to 40 mg/kg or 15 to 30 mg/kg. In another preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. Even more preferably, the anti-N3pGlu Aβ antibody is selected from Table A.

In another embodiment the present invention provides for a use of an anti-N3pGlu Aβ antibody for the manufacture of a medicament for the treatment of prodromal AD, mild AD, moderate AD or severe AD, wherein the medicament comprises an induction dose of 10 to 60 mg/kg of an anti-N3pGlu Aβ antibody administered to a patient for a period of 6 months or less. Particularly, the present invention provides for a use of an anti-N3pGlu Aβ antibody for the manufacture of a medicament for the treatment of prodromal AD, mild AD, moderate AD or severe AD, wherein the medicament comprises a one-time induction dose of 10 to 60 mg/kg of an anti-N3pGlu Aβ antibody administered to a patient for a period of 6 months or less. In another more particular embodiment, the present invention provides for a use of an anti-N3pGlu Aβ antibody for the manufacture of a medicament for the treatment of prodromal AD, mild AD, moderate AD or severe AD, wherein the medicament comprises an induction dose of 10 to 60 mg/kg of an anti-N3pGlu Aβ antibody administered to a patient every two weeks for a period of 6 months or less. In another more particular embodiment, the present invention provides for a use of an anti-N3pGlu Aβ antibody for the manufacture of a medicament for the treatment of prodromal AD, mild AD, moderate AD or severe AD, wherein the medicament comprises an induction dose of 10 to 60 mg/kg of an anti-N3pGlu Aβ antibody administered to a patient monthly for a period of 6 months or less. In a preferred embodiment of the invention the one-time, biweekly and monthly induction dose administered to a patient is 20 to 40 mg/kg or 15 to 30 mg/kg. In another preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. Even more preferably, the anti-N3pGlu Aβ antibody is selected from Table A.

In another embodiment the present invention provides for a use of an anti-N3pGlu Aβ antibody for the manufacture of a medicament for preventing or slowing cognitive or functional decline in a patient diagnosed with a condition selected from clinical or pre-clinical Alzheimer's disease, Down's syndrome, and clinical or pre-clinical cerebral amyloid angiopathy, wherein the medicament comprises an induction dose of 10 to 60 mg/kg of an anti-N3pGlu Aβ antibody administered to a patient for a period of 6 months or less. Particularly, the present invention provides for a use of an anti-N3pGlu Aβ antibody for the manufacture of a medicament for preventing or slowing cognitive decline in a patient diagnosed with a condition selected from clinical or pre-clinical Alzheimer's disease, Down's syndrome, and clinical or pre-clinical cerebral amyloid angiopathy, wherein the medicament comprises a one-time induction dose of 10 to 60 mg/kg of an anti-N3pGlu Aβ antibody administered to a patient for a period of 6 months or less. In another more particular embodiment, the present invention provides for a use of an anti-N3pGlu Aβ antibody for preventing or slowing cognitive decline in a patient diagnosed with a condition selected from clinical or pre-clinical Alzheimer's disease, Down's syndrome, and clinical or pre-clinical cerebral amyloid angiopathy, wherein the medicament comprises an induction dose of 10 to 60 mg/kg of an anti-N3pGlu Aβ antibody administered every two weeks to a patient for a period of 6 months or less. In another more particular embodiment, the present invention provides for a use of an anti-N3pGlu Aβ antibody for preventing or slowing cognitive decline in a patient diagnosed with a condition selected from clinical or pre-clinical Alzheimer's disease, Down's syndrome, and clinical or pre-clinical cerebral amyloid angiopathy, wherein the medicament comprises a one-time induction dose of 10 to 60 mg/kg of an anti-N3pGlu Aβ antibody administered to a patient monthly for a period of 6 months or less. In a preferred embodiment of the invention the one-time, biweekly and monthly induction dose administered to a patient is 20 to 40 mg/kg or 15 to 30 mg/kg. In another preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. Even more preferably, the anti-N3pGlu Aβ antibody is selected from Table A.

In another embodiment the present invention provides for a use of an anti-N3pGlu Aβ antibody for the manufacture of a medicament for treating asymptomatic patients known to have an Alzheimer's disease causing genetic mutation, wherein the medicament is administered to a patient at a dosage of 10 to 60 mg/kg of the anti-N3pGlu Aβ antibody for a period of 6 months or less. Particularly, the present invention provides for a use of an anti-N3pGlu Aβ antibody for the manufacture of a medicament for treating asymptomatic patients known to have an Alzheimer's disease causing genetic mutation, wherein the medicament comprises a one-time induction dose of 10 to 60 mg/kg of an anti-N3pGlu Aβ antibody administered to a patient for a period of 6 months or less. In another more particular embodiment, the present invention provides for a use of an anti-N3pGlu Aβ antibody treating asymptomatic patients known to have an Alzheimer's disease causing genetic mutation, wherein the medicament comprises an induction dose of 10 to 60 mg/kg of an anti-N3pGlu Aβ antibody administered to a patient every two weeks for a period of 6 months or less. In another more particular embodiment, the present invention provides for a use of an anti-N3pGlu Aβ antibody treating asymptomatic patients known to have an Alzheimer's disease causing genetic mutation, wherein the medicament comprises an induction dose of 10 to 60 mg/kg of an anti-N3pGlu Aβ antibody administered to a patient monthly for a period of 6 months or less. In a preferred embodiment of the invention the one-time, biweekly and monthly induction dose administered to a patient is 20 to 40 mg/kg or 15 to 30 mg/kg. In another preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. Even more preferably, the anti-N3pGlu Aβ antibody is selected from Table A.

In another embodiment the present invention provides for a use of an anti-N3pGlu Aβ antibody for the manufacture of a medicament for reducing Aβ deposits in the brain of a patient, wherein the medicament comprises an induction dose of 10 to 60 mg/kg of an anti-N3pGlu Aβ antibody administered to a patient for a period of 6 months or less, and wherein the Aβ deposit in the brain of a patient is reduced by 35-100% within 6 months post induction dose treatment. Particularly the present invention provides for a use of an anti-N3pGlu Aβ antibody for the manufacture of a medicament for reducing Aβ deposits in the brain of a patient, wherein the medicament comprises a one-time induction dose of 10 to 60 mg/kg of an anti-N3pGlu Aβ antibody administered to a patient for a period of 6 months or less, and wherein the Aβ deposit in the brain of a patient is reduced by 35-100% within 6 months post induction dose treatment. In another more particular embodiment, the present invention provides for a use of an anti-N3pGlu Aβ antibody for the manufacture of a medicament for reducing Aβ deposits in the brain of a patient, wherein the medicament comprises an induction dose of 10 to 60 mg/kg of an anti-N3pGlu Aβ antibody administered to a patient every two weeks for a period of 6 months or less, and wherein the Aβ deposit in the brain of a patient is reduced by 35-100% within 6 months post induction dose treatment. In another more particular embodiment, the present invention provides for a use of an anti-N3pGlu Aβ antibody for the manufacture of a medicament for reducing Aβ deposits in the brain of a patient, wherein the medicament comprises an induction dose of 10 to 60 mg/kg of an anti-N3pGlu Aβ antibody administered to a patient monthly for a period of 6 months or less, and wherein the Aβ deposit in the brain of a patient is reduced by 35-100%/o within 6 months post induction dose treatment. In a preferred embodiment of the invention the one-time, biweekly and monthly induction dose administered to a patient is 20 to 40 mg/kg or 15 to 30 mg/kg. In another preferred embodiment of the present invention, the one-time induction dose administered to a patient is 10 mg/kg, 15 mg/kg, 20 mg/kg or 40 mg/kg. In an alternative preferred embodiment of the present invention, the biweekly and monthly induction dose administered to a patient is 10 mg/kg, 15 mg/kg, 20 mg/kg or 40 mg/kg for a period of 6 months. Even more preferably, the anti-N3pGlu Aβ antibody is selected from Table A.

As used herein, "anti-N3pglu Aβ antibody" refers to an antibody that binds preferentially to N3pGlu Aβ over Aβ$_{1-40}$ or Aβ$_{1-42}$. The sequence of N3pGlu Aβ is the amino acid sequence of SEQ ID NO: 31. In particular embodiments, the anti-N3pGlu Aβ antibodies comprise amino acid sequences listed in Table A. More specifically, the anti-N3pGlu Aβ antibodies of the present invention comprises a light chain variable region (LCVR) and a heavy chain variable region (HCVR), wherein said LCVR comprises LCDR1, LCDR2 and LCDR3 and HCVR comprises HCDR1, HCDR2 and HCDR3 which are selected from the group consisting of:

a) LCDR1 is SEQ ID. NO: 17, LCDR2 is SEQ ID. NO: 18, LCDR3 is SEQ ID. NO: 19, HCDR1 is SEQ ID. NO: 20, HCDR2 is SEQ ID: NO: 22, and HCDR3 is SEQ ID. NO: 23: and
b) LCDR1 is SEQ ID. NO: 17, LCDR2 is SEQ ID. NO: 18, LCDR3 is SEQ ID. NO: 19, HCDR1 is SEQ ID. NO: 21, HCDR2 is SEQ ID. NO: 22, and HCDR3 is SEQ ID. NO: 24;
c) LCDR1 is SEQ ID. NO: 17, LCDR2 is SEQ ID. NO: 18, LCDR3 is SEQ ID. NO: 19, HCDR1 is SEQ ID. NO: 36, HCDR2 is SEQ ID. NO: 22, and HCDR3 is SEQ ID. NO: 37;
d) LCDR1 is SEQ ID. NO: 4, LCDR2 is SEQ ID. NO: 6, LCDR3 is SEQ ID. NO: 7, HCDR1 is SEQ ID. NO: 1, HCDR2 is SEQ ID. NO: 2, and HCDR3 is SEQ ID. NO: 3; and
e) LCDR1 is SEQ ID. NO: 4, LCDR2 is SEQ ID. NO: 5, LCDR3 is SEQ ID. NO: 7, HCDR1 is SEQ ID. NO: 1, HCDR2 is SEQ ID. NO: 2, and HCDR3 is SEQ ID. NO: 3.

In other embodiments, the anti-N3pGlu Aβ antibodies of the present invention comprise a light chain variable region (LCVR) and a heavy chain variable region (HCVR), wherein said LCVR and HCVR are selected from the group consisting of:

a) LCVR of SEQ ID NO: 25 and HCVR of SEQ ID NO: 26;
b) LCVR of SEQ ID NO: 25 and HCVR of SEQ ID NO: 27;
c) LCVR of SEQ ID NO: 32 and HCVR of SEQ ID NO: 34;
d) LCVR of SEQ ID NO: 9 and HCVR of SEQ ID NO: 8: and
e) LCVR of SEQ ID NO: 10 and HCVR of SEQ ID NO: 8.

In further embodiments, the anti-N3pGlu Aβ antibody comprises a light chain (LC) and a heavy chain (HC), wherein said LC and HC are selected from the group consisting of: a) LC of SEQ ID NO: 28 and HC of SEQ ID NO: 29;
b) LC of SEQ ID NO: 28 and HC of SEQ ID NO: 30;
c) LC of SEQ ID NO: 33 and HC of SEQ ID NO: 35;
d) LC of SEQ ID NO: 12 and HC of SEQ ID NO: 11; and
e) LC of SEQ ID NO: 13 and HC of SEQ ID NO: 11.

In other embodiments, the anti-N3pGlu Aβ antibody comprises two light chains (LC) and two heavy chains (HC), wherein each LC and each HC are selected from the group consisting of a) LC of SEQ ID NO: 28 and HC of SEQ ID NO: 29;
b) LC of SEQ ID NO: 28 and HC of SEQ ID NO: 30;
c) LC of SEQ ID NO: 33 and HC of SEQ ID NO: 35;
d) LC of SEQ ID NO: 12 and HC of SEQ ID NO: 11; and
e) LC of SEQ ID NO: 13 and HC of SEQ ID NO: 11.

In some embodiments, the anti-N3pGlu Aβ antibody comprises Antibody I, which has a light chain (LC) and a heavy chain (HC) of SEQ ID NOs: 12 and 11 respectively. Antibody I further has a light chain variable region (LCVR) and a heavy chain variable region (HCVR) of SEQ ID NOs: 9 and 8 respectively. The HCVR of Antibody I further comprises HCDR1 of SEQ ID NO: 1, HCDR2 of SEQ ID NO: 2, and HCDR3 of SEQ ID NO: 3. The LCVR of Antibody I further comprises LCDR1 of SEQ ID NO: 4, LCDR2 of SEQ ID NO: 6 and LCDR3 of SEQ ID NO: 7 respectively.

In some embodiments, the anti-N3pGlu Aβ antibody comprises Antibody II, which has a light chain (LC) and a heavy chain (HC) of SEQ ID NOs: 13 and 11 respectively. Antibody II further has a light chain variable region (LCVR) and a heavy chain variable region (HCVR) of SEQ ID NOs: 10 and 8 respectively. The HCVR of Antibody II further comprises HCDR1 of SEQ ID NO: 1, HCDR2 of SEQ ID NO: 2, and HCDR3 of SEQ ID NO: 3. The LCVR of Antibody II further comprises LCDR1 of SEQ ID NO: 4, LCDR2 of SEQ ID. NO. 5, and LCDR3 of SEQ ID NO: 7 respectively.

In some embodiments, the anti-N3pGlu Aβ antibody comprises B12L, which has a light chain (LC) and a heavy chain (HC) of SEQ ID NOs: 28 and 29 respectively. B12L further has a light chain variable region (LCVR) and a heavy chain variable region (HCVR) of SEQ ID NOs: 25 and 26 respectively. The HCVR of B12L further comprises HCDR1 of SEQ ID NO: 20. HCDR2 of SEQ ID NO: 22 and HCDR3 of SEQ ID NO: 23. The LCVR of B12L further comprises LCDR1 of SEQ ID NO. 17, LCDR2 of SEQ ID NO: 18 and LCDR3 of SEQ ID NO: 19 respectively.

In some embodiments, the anti-N3pGlu Aβ antibody comprises R17L which has a light chain (LC) and a heavy chain (HC) of SEQ ID NOs: 28 and 30 respectively. R17L further has a light chain variable region (LCVR) and a heavy chain variable region (HCVR) of SEQ ID NOs: 25 and 27 respectively. The HCVR of R17L further comprises HCDR1 of SEQ ID NO: 21, HCDR2 of SEQ ID NO: 22 and HCDR3 of SEQ ID NO: 24. The LCVR of R17L further comprises LCDR1 of SEQ ID NO. 17, LCDR2 of SEQ ID NO: 18 and LCDR3 of SEQ ID NO: 19 respectively.

In some embodiments, the anti-N3pGlu Aβ antibody comprises hE8L which has a light chain (LC) and a heavy chain (HC) of SEQ ID NOs: 33 and 35 respectively, hE8L further has a light chain variable region (LCVR) and a heavy chain variable region (HCVR) of in SEQ ID NOs: 32 and 34 respectively. The HCVR of hE8L further comprises HCDR1 of SEQ ID NO: 36, HCDR2 of SEQ ID NO: 22 and HCDR3 of SEQ ID NO: 37. The LCVR of hE8L further comprises LCDR1 of SEQ ID NO. 17, LCDR2 of SEQ ID NO. 18 and LCDR3 of SEQ ID NO: 19 respectively.

In some embodiments, the anti-N3pGlu Aβ antibody comprises Antibody VI which has a light chain variable region (LCVR) and a heavy chain variable region (HCVR) of SEQ ID NOs: 39 and 40 respectively.

In some embodiments, the anti-N3pGlu Aβ antibody comprises Antibody VII which has a light chain variable region (LCVR) and a heavy chain variable region (HCVR) of SEQ ID NOs: 41 and 42 respectively.

In some embodiments, the anti-N3pGlu Aβ antibody comprises Antibody VIII which has a light chain variable region (LCVR) and a heavy chain variable region (HCVR) of SEQ ID NOs: 43 and 44 respectively.

In some embodiments, the anti-N3pGlu Aβ antibody comprises Antibody IX which has a light chain variable region (LCVR) and a heavy chain variable region (HCVR) of SEQ ID NOs: 45 and 46 respectively.

In some embodiments, the anti-N3pGlu Aβ antibody comprises Antibody X which has a light chain variable region (LCVR) and a heavy chain variable region (HCVR) of SEQ ID NOs: 47 and 48 respectively.

In some embodiments, the anti-N3pGlu Aβ antibody comprises Antibody XI which has a light chain variable region (LCVR) and a heavy chain variable region (HCVR) of SEQ ID NOs: 49 and 50 respectively.

In some embodiments, the anti-N3pGlu Aβ antibody comprises Antibody XII which has a light chain variable region (LCVR) and a heavy chain variable region (HCVR) of SEQ ID NOs: 51 and 52 respectively.

In some embodiments, the anti-N3pGlu Aβ antibody comprises Antibody XIII which has a light chain variable region (LCVR) and a heavy chain variable region (HCVR) of SEQ ID NOs: 53 and 54 respectively.

A person of skill in the art would recognize that an embodiment of the present invention provides a method of treating or preventing clinical or pre-clinical Alzheimer's disease. Down's syndrome, and clinical or pre-clinical CAA in a patient positive for amyloid deposits, comprising administering to a patient a one-time, biweekly or monthly induction dose of an anti-N3pGlu Aβ antibody for a period of 6 months or less, wherein the anti-N3pGlu Aβ antibody comprises a light chain variable region (LCVR) and a heavy chain variable region (HCVR), wherein said LCVR and HCVR are selected from the group consisting of:
a) LCVR of SEQ ID NO: 25 and HCVR of SEQ ID NO: 26;
b) LCVR of SEQ ID NO: 25 and HCVR of SEQ ID NO: 27;
c) LCVR of SEQ ID NO: 32 and HCVR of SEQ ID NO: 34;
d) LCVR of SEQ ID NO: 9 and HCVR of SEQ ID NO: 8; and
e) LCVR of SEQ ID NO: 10 and HCVR of SEQ ID NO: 8.

Preferably the anti-N3pGlu Aβ antibody comprises a LCVR of SEQ ID NO: 25 and HCVR of SEQ ID NO: 26. More preferably the anti-N3pGlu Aβ antibody is administered one-time or biweekly. Even more preferably, the one-time or biweekly dose results in 35-100% reduction in Aβ deposit in the brain of the patient within 6 months of administration of the induction dose.

In another particular embodiments, the present invention provides a method of treating or preventing clinical or pre-clinical Alzheimer's disease, Down's syndrome, and clinical or pre-clinical CAA in a patient positive for amyloid deposits, comprising administering to a patient a one-time, biweekly or monthly induction dose of an anti-N3pGlu Aβ antibody for a period of 6 months or less, wherein the anti-N3pGlu Aβ antibody comprises a light chain (LC) and a heavy chain (HC), wherein said LC and HC are selected from the group consisting of:
a) LC of SEQ ID NO: 28 and HC of SEQ ID NO: 29;
b) LC of SEQ ID NO: 28 and HC of SEQ ID NO: 30;
c) LC of SEQ ID NO: 33 and HC of SEQ ID NO: 35;
d) LC of SEQ ID NO: 12 and HC of SEQ ID NO: 11; and
e) LC of SEQ ID NO: 13 and HC of SEQ ID NO: 11.

Preferably the anti-N3pGlu Aβ antibody comprises a LC of SEQ ID NO: 28 and HC of SEQ ID NO: 29. More preferably the anti-N3pGlu Aβ antibody is administered one-time or biweekly. Even more preferably, the one-time or biweekly dose results in 35-100% reduction in Aβ deposit in the brain of the patient within 6 months of administration of the induction dose.

A further embodiment provides a method of treating or preventing clinical or pre-clinical Alzheimer's disease, Down's syndrome, and clinical or pre-clinical CAA in a patient positive for amyloid deposits, comprising administering to a patient a one-time, biweekly or monthly induction dose of an anti-N3pGlu Aβ antibody for a period of 6 months or less, wherein the anti-N3pGlu Aβ antibody comprises two light chains (LC's) and two heavy chains (HC's), wherein each LC and HC is selected from the group consisting of:
   a) LC of SEQ ID NO: 28 and HC of SEQ ID NO: 29;
   b) LC of SEQ ID NO: 28 and HC of SEQ ID NO: 30;
   c) LC of SEQ ID NO: 33 and HC of SEQ ID NO: 35;
   d) LC of SEQ ID NO: 12 and HC of SEQ ID NO: 11; and
   e) LC of SEQ ID NO: 13 and HC of SEQ ID NO: 11.

Preferably the anti-N3pGlu Aβ antibody comprises a two LC's of SEQ ID NO: 28 and HC's of SEQ ID NO: 29. More preferably the anti-N3pGlu Aβ antibody is administered one-time or biweekly. Even more preferably, the one-time or biweekly dose results in 35-100% reduction in Aβ deposit in the brain of the patient within 6 months of administration of the induction dose.

The present invention also provides a method of treating or preventing clinical or pre-clinical Alzheimer's disease, Down's syndrome, and clinical or pre-clinical CAA in a patient positive for amyloid deposits, comprising administering to a patient a one-time, biweekly or monthly induction dose of 10 to 60 mg/kg of an anti-N3pGlu Aβ antibody for a period of 6 month or less, wherein the anti-N3pGlu Aβ antibody comprises a light chain variable region (LCVR) and a heavy chain variable region (HCVR), wherein said LCVR and HCVR are selected from the group consisting of:
   a) LCVR of SEQ ID NO: 25 and HCVR of SEQ ID NO: 26;
   b) LCVR of SEQ ID NO: 25 and HCVR of SEQ ID NO: 27;
   c) LCVR of SEQ ID NO: 32 and HCVR of SEQ ID NO: 34;
   d) LCVR of SEQ ID NO: 9 and HCVR of SEQ ID NO: 8; and
   e) LCVR of SEQ ID NO: 10 and HCVR of SEQ ID NO: 8.

Preferably the anti-N3pGlu Aβ antibody comprises a LCVR of SEQ ID NO: 25 and HCVR of SEQ ID NO: 26. More preferably, the one-time, biweekly (every two weeks) and monthly induction dose administered to a patient is 10 mg/kg, 15 mg/kg, 20 mg/kg, 40 mg/kg, 20 to 40 mg/kg or 15 to 30 mg/kg. Even more preferably the induction dose of the anti-N3pGlu Aβ antibody is administered one-time or biweekly. Even more preferably, the one-time or biweekly dose results in 35-100% reduction in Aβ deposit in the brain of the patient within 6 months of administration of the induction dose.

In an embodiment, the present invention provides a method of treating or preventing clinical or pre-clinical Alzheimer's disease, Down's syndrome, and clinical or pre-clinical CAA in a patient positive for amyloid deposits, comprising administering to a patient a one-time, biweekly or monthly induction dose of 10 to 60 mg/kg of an anti-N3pGlu Aβ antibody for a period of 6 month or less, wherein the anti-N3pGlu Aβ antibody comprises a light chain (LC) and a heavy chain (HC), wherein said LC and HC are selected from the group consisting of:
   a) LC of SEQ ID NO: 28 and HC of SEQ ID NO: 29;
   b) LC of SEQ ID NO: 28 and HC of SEQ ID NO: 30;
   c) LC of SEQ ID NO: 33 and HC of SEQ ID NO: 35;
   d) LC of SEQ ID NO: 12 and HC of SEQ ID NO: 11; and
   e) LC of SEQ ID NO: 13 and HC of SEQ ID NO: 11.

Preferably the anti-N3pGlu Aβ antibody comprises a LC of SEQ ID NO: 28 and a HC of SEQ ID NO: 29. More preferably, the one-time, biweekly (every two weeks) and monthly induction dose administered to a patient is 10 mg/kg, 15 mg/kg, 20 mg/kg, 40 mg/kg, 20 to 40 mg/kg or 15 to 30 mg/kg. Even more preferably the induction dose of the anti-N3pGlu Aβ antibody is administered one-time or biweekly. Even more preferably, the one-time or biweekly dose results in 35-100% reduction in Aβ deposit in the brain of the patient within 6 months of administration of the induction dose.

The present invention also provides a method of treating or preventing clinical or pre-clinical Alzheimer's disease, Down's syndrome, and clinical or pre-clinical CAA in a patient positive for amyloid deposits, comprising administering to a patient a one-time, biweekly or monthly induction dose of 10 to 60 mg/kg of an anti-N3pGlu Aβ antibody for a period of 6 month or less, wherein the anti-N3pGlu Aβ antibody comprises two light chains (LC) and two heavy chains (HC), wherein each LC and HC is selected from the group consisting of:
   a) LC of SEQ ID NO: 28 and HC of SEQ ID NO: 29;
   b) LC of SEQ ID NO: 28 and HC of SEQ ID NO: 30;
   c) LC of SEQ ID NO: 33 and HC of SEQ ID NO: 35;
   d) LC of SEQ ID NO: 12 and HC of SEQ ID NO: 11; and
   e) LC of SEQ ID NO: 13 and HC of SEQ ID NO: 11.

Preferably the anti-N3pGlu Aβ antibody comprises two LC's of SEQ ID NO: 28 and two HC's of SEQ ID NO: 29. More preferably, the one-time, biweekly (every two weeks) and monthly induction dose administered to a patient is 10 mg/kg, 15 mg/kg, 20 mg/kg, 40 mg/kg, 20 to 40 mg/kg or 15 to 30 mg/kg. Even more preferably the induction dose of the anti-N3pGlu Aβ antibody is administered one-time or biweekly. Even more preferably, the one-time or biweekly dose results in 35-100% reduction in Aβ deposit in the brain of the patient within 6 months of administration of the induction dose.

One of ordinary skill in the art will appreciate and recognize that "anti-N3pGlu Aβ antibody", and the specific antibodies, "hE8L", "B12L" and "R17L" are identified and disclosed along with methods for making and using said antibodies by one of ordinary skill in the art as set forth in U.S. Pat. No. 8,679,498 B2, entitled "Anti-N3pGlu Amyloid Beta Peptide Antibodies and Uses Thereof", issued Mar. 25, 2014 (U.S. Ser. No. 13/810,895). See for example Table 1 of U.S. Pat. No. 8,679,498 B2. Each of these three antibodies (e.g., "hE8L", "B12L" and "R17L") may be used as the anti-N3pGlu Aβ antibody of the present invention. One of ordinary skill in the art will appreciate and recognize that "anti-N3pGlu Aβ antibody", and the specific antibodies, "Antibody VI", "Antibody VII", "Antibody VIII", and "Antibody IX" are identified and disclosed along with methods for making and using said antibodies by one of ordinary skill in the art as set forth in WO2010/009987A2, entitled "Diagnosed Antibody Assay". Each of these four antibodies (e.g., "Antibody VI", "Antibody VII", "Antibody VIII", and "Antibody IX") may be used as the anti-N3pGlu Aβ antibody of the present invention.

One of ordinary skill in the art will appreciate and recognize that "anti-N3pGlu Aβ antibody", and the specific antibodies, "Antibody X" and "Antibody XI" are identified and disclosed along with methods for making and using said antibodies by one of ordinary skill in the art as set forth in WO 2011/151076 A2, entitled "Monoclonal Antibodies Targeting AD Monoclonal Antibodies". Each of these two antibodies (e.g. "Antibody X" and "Antibody XI") may be used as the anti-N3pGlu Aβ antibody of the present invention.

One of ordinary skill in the art will appreciate and recognize that "anti-N3pGlu Aβ antibody", and the specific antibodies, "Antibody XII" and "Antibody XIII" are identified and disclosed along with methods for making and using said antibodies by one of ordinary skill in the art as set forth in WO 2012/136552A1, entitled "Antibodies Specific to Pyroglutamated Aβ". Each of these two antibodies (e.g., "Antibody XII" and "Antibody XIII") may be used as the anti-N3pGlu Aβ antibody of the present invention.

One of ordinary skill in the art will appreciate and recognize that "Aβ antibody", and the specific antibody, "aducanumab" is identified and disclosed along with methods for making and using said antibody by one of ordinary skill in the art as set forth in WO14089500A1, entitled "A Method of Reducing Brain Amyloid Plaques Using Anti-AD Antibodies", published Jun. 12, 2014. This may be used as the Aβ antibody of the present invention.

One of ordinary skill in the art will appreciate and recognize that "Aβ antibody", and the specific antibody, "gantenerumab" is identified and disclosed along with methods for making and using said antibody by one of ordinary skill in the art as set forth in WO2007068429, entitled "Antibodies Against Amyloid Beta 4 with Glycosylated in the Variable Region", published Jun. 21, 2007. This may be used as the Aβ antibody of the present invention.

One of ordinary skill in the art will appreciate and recognize that "Aβ antibody", and the specific antibody, "crenezumab" is identified and disclosed along with methods for making and using said antibody by one of ordinary skill in the art as set forth in 2015120280A1, entitled "Methods of treating alzheimer's disease", published Aug. 13, 2015. This may be used as the Aβ antibody of the present invention.

One of ordinary skill in the art will appreciate and recognize that "Aβ antibody", and the specific antibody, "BAN 2401" is identified and disclosed along with methods for making and using said antibody by one of ordinary skill in the art as set forth in U.S. Pat. No. 8,025,878 B2, entitled "Protofibril selective antibodies and the use thereof", issued Sep. 27, 2011. This may be used as the Aβ antibody of the present invention.

One of ordinary skill in the art will appreciate and recognize that "Aβ antibody", and the specific antibody, "solancezumab" is identified and disclosed along with methods for making and using said antibody by one of ordinary skill in the art as set forth in U.S. Pat. No. 7,195,761 B2, entitled "Humanized Antibodies that Sequester ABeta Peptide", issued Mar. 27, 2007. This may be used as the Aβ antibody of the present invention.

One of ordinary skill in the art will appreciate and recognize that "Aβ antibody", and the specific antibody. "Antibody XIV" is identified and disclosed along with methods for making and using said antibody by one of ordinary skill in the an as set forth in U.S. Pat. No. 8,066,999 B1, entitled "Pegylated Aβ FAB", issued Nov. 29, 2011 (U.S. application Ser. No. 12/521,309). This may be used as the Aβ antibody of the present invention.

The compound of formula:

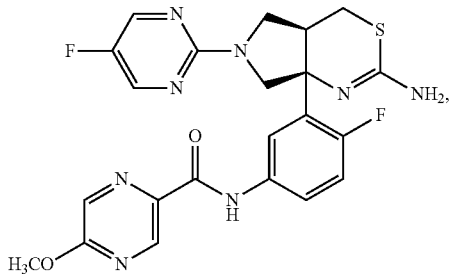 [SMILES: COc1cnc(C(=O)Nc2ccc(F)c([C@]34CN(c5ncc(F)cn5)C[C@H]3CSC(N)=N4)c2)cn1]

or a pharmaceutically acceptable salt thereof, is disclosed as a BACE inhibitor and can be prepared by one of ordinary skill in the art as set forth in U.S. Pat. No. 8,841,293 B1, entitled "Tetrahydropyrrolothiazine Compounds", issued Sep. 23, 2014 (U.S. application Ser. No. 14/195,897); see in particular. Example 4, N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide. The tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide can be prepared by one of ordinary skill in the art as set forth in PCT/US2016/014423. The crystalline form of N-[3-[(4aR,7aS)-2-amino-6-(5-fluoropyrimidin-2-yl)-4,4a,5,7-tetrahydropyrrolo[3,4-d[1,3]thiazin-7a-yl]-4-fluoro-phenyl]-5-methoxy-pyrazine-2-carboxamide can be prepared by one of ordinary skill in the art as set forth in WO 2016/043996, entitled "A Tetrahydropyrrolo[3,4-D][1,3]Thiazine-Derivative as BACE Inhibitor".

The compound of the formula:

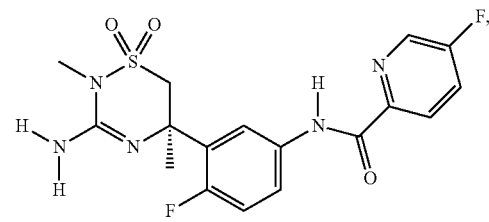 [SMILES: CN1C(N)=N[C@](C)(c2cc(NC(=O)c3ccc(F)cn3)ccc2F)CS1(=O)=O]

or a pharmaceutically acceptable salt thereof, is disclosed as a BACE inhibitor and can be prepared by one of ordinary skill in the art as set forth in U.S. Pat. No. 8,729,071 B1, entitled "Iminothiadiazine Dioxide Compounds As BACE Inhibitors. Compositions and Their Use" issued May 20, 2014. Crystalline forms and crystalline forms of the tosylate salt of N-[3-[(5R-3-Amino-5,6-dihydro-2,5-dimethyl-1,1-dioxido-2H-1,2,4-thiadiazin-5-yl]-4-fluorophenyl]-5-fluoro-2-pyridinecarboxamide, verubecestat, are disclosed and can be prepared by one of ordinary skill in the art as set forth in WO2016/053767, entitled "Novel Crystalline forms of a BACE Inhibitor, Compositions, and their Use".

In addition, amino acid sequences for certain anti-N3pGlu Aβ antibodies used in the present invention are provided below in Table A:

TABLE A

Antibody Amino Acid Sequences

| Anti-N3pGlu Antibody | LCVR | HCVR | LC | HC |
|---|---|---|---|---|
| Antibody I | 9 | 8 | 12 | 11 |
| Antibody II | 10 | 8 | 13 | 11 |
| Antibody III (B12L) | 25 | 26 | 28 | 29 |
| Antibody IV (R17L) | 25 | 27 | 28 | 30 |
| Antibody V(hE8L) | 32 | 34 | 31 | 35 |
| Antibody VI (5-5-6) | 39 | 40 | | |
| Antibody VII (6-1-6) | 41 | 42 | | |
| Antibody VIII(17-4-3) | 43 | 44 | | |
| Antibody IX (24-2-3) | 45 | 46 | | |
| Antibody X (9D5H6) | 47 | 48 | | |
| Antibody XI (8C4) | 49 | 50 | | |
| Antibody XII (5C9 AAb1h) | 51 | 52 | | |
| Antibody XIII (2E83 (LuAb2h) | 53 | 54 | | |

With respect to "Antibody 1", "Antibody 11", "Antibody III", "Antibody IV", and "Antibody V", additional amino acid sequences for such antibodies are provided in Table B:

TABLE B

Antibody CDR Amino Acid Sequences
Antibody SEQ ID NOs

| Antibody | LCDR1 | LCDR2 | LCDR3 | HCDR1 | HCDR2 | HCDR3 |
|---|---|---|---|---|---|---|
| I | 4 | 6 | 7 | 1 | 2 | 3 |
| II | 4 | 5 | 7 | 1 | 2 | 3 |
| III (B12L) | 17 | 18 | 19 | 20 | 22 | 23 |
| IV (R17L) | 17 | 18 | 19 | 21 | 22 | 24 |
| V (hE8L) | 17 | 18 | 19 | 36 | 22 | 37 |

As used herein, an "antibody" is an immunoglobulin molecule comprising two Heavy Chain (HC) and two Light Chain (LC) interconnected by disulfide bonds. The amino terminal portion of each LC and HC includes a variable region responsible for antigen recognition via the complementarity determining regions (CDRs) contained therein. The CDRs are interspersed with regions that are more conserved, termed framework regions. Assignment of amino acids to CDR domains within the LCVR and HCVR regions of the antibodies of the present invention is based on the following: Kabat numbering convention (Kabat, et al., Ann. N.Y. Acad. Sci. 190:382-93 (1971): Kabat et al., Sequences of Proteins of Immunological Interest, Fifth Edition, U.S. Department of Health and Human Services, NIH Publication No. 91-3242 (1991)), and North numbering convention (North et al., A New Clustering of Antibody CDR Loop Conformations, Journal of Molecular Biology, 406:228-256 (2011)). Following the above method, the CDRs of the present invention were determined (Table B).

The anti-N3pGlu Aβ antibodies of the present invention include kappa LC and IgG HC. In a particular embodiment, the anti-N3pglu Aβ antibodies of the present invention are of the human IgG1 isotype.

The antibodies of the present invention are monoclonal antibodies ("mAbs"). Monoclonal antibodies can be produced, for example, by hybridoma technologies, recombinant technologies, phage display technologies, synthetic technologies, e.g., CDR-grafting, or combinations of such or other technologies known in the art. The monoclonal antibodies of the present invention are human or humanized. Humanized antibodies can be engineered to contain one or more human framework regions (or substantially human framework regions) surrounding CDRs derived from a non-human antibody. Human framework germline sequences can be obtained from ImunoGeneTics (INGT) via their website, http://imgt.cines.fr, or from *The Immunoglobulin FactsBook* by Marie-Paule Lefranc and Gerard Lefranc, Academic Press, 2001, ISBN 012441351. Techniques for generating human or humanized antibodies are well known in the art. In another embodiment of the present invention, the antibody, or the nucleic acid encoding the same, is provided in isolated form. As used herein, the term "isolated" refers to a protein, peptide or nucleic acid that is not found in nature and is free or substantially free from other macromolecular species found in a cellular environment. "Substantially free", as used herein, means the protein, peptide or nucleic acid of interest comprises more than 80% (on a molar basis) of the macromolecular species present, preferably more than 90% and more preferably more than 95%.

The anti-N3pGlu Aβ antibody of the present invention is administered as a pharmaceutical composition. The pharmaceutical composition comprising an antibody of the present invention can be administered to a patient at risk for, or exhibiting, diseases or disorders as described herein by parental routes (e.g., subcutaneous, intravenous, intraperitoneal, intramuscular). Subcutaneous and intravenous routes are preferred.

The terms "treatment," "treating" or "to treat" and the like include restraining, slowing or stopping the progression or severity of an existing symptom, condition, disease, or disorder in a patient. The term "patient" refers to a human.

The term "prevention" means prophylactic administration of the antibody of the present invention to an asymptomatic patient or a patient with pre-clinical Alzheimer's disease to prevent onset or progression of the disease.

The terms "disease characterized by deposition of Aβ' or a disease characterized by Aβ deposits" are used interchangeably and refer to a disease that is pathologically characterized by Aβ deposits in the brain or in brain vasculature. This includes diseases such as Alzheimer's disease. Down's syndrome, and cerebral amyloid angiopathy. A clinical diagnosis, staging or progression of Alzheimer's disease can be readily determined by the attending diagnostician or health care professional, as one skilled in the art, by using known techniques and by observing results. This generally includes some form of brain plaque imagining, mental or cognitive assessment (e.g. Clinical Dementia Rating—summary of boxes (CDR-SB), Mini-Mental State Exam (MMSE) or Alzheimer's Disease Assessment Scale-Cognitive (ADAS-Cog)) or functional assessment (e.g. Alzheimer's Disease Cooperative Study-Activities of Daily Living (ADCS-ADL). The cognitive and functional assessment can be used to determine changes in a patients cognition (e.g. cognitive decline) and function (e.g. functional decline). "Clinical Alzheimer's disease" as used herein is a diagnosed stage of Alzheimer's disease. It includes conditions diagnosed as prodromal Alzheimer's disease, mild Alzheimer's disease, moderate Alzheimer's disease and severe Alzheimer's disease. The term "pre-clinical Alzheimer's disease" is a stage that precedes clinical Alzheimer's disease, where measurable changes in biomarkers (such as CSF Aβ42 levels or deposited brain plaque by amyloid PET) indicate the earliest signs of a patient with Alzheimer's pathology, progressing to clinical Alzheimer's disease. This is usually before symptoms such as memory loss and confusion are noticeable. Pre-clinical Alzheimer's disease also includes pre-symptomatic autosomal dominant carriers, as well as patients with higher risk for developing AD by virtue of carrying one or two APOE e4 alleles.

For patients undergoing brain plaque imaging, a patient is positive for amyloid deposits when amyloid is detected in the brain by methods such as amyloid imaging with radiolabeled PET compounds. An example of one such amyloid PET imaging compound is florbetapir F 18, which bind with high specificity to amyloid plaques. The chemical formula of florbetapir F 18 is $C_{20}H_{25}{}^{18}FN_2O_3$. Amyloid imaging with radiolabeled PET compounds can be used to determine if Aβ deposit in the brain of a human patient is reduced by 35-100% within 6 months post induction treatment. A person of skill in the art can correlate the standardized uptake value ratio (SUVR) values obtained from amyloid imaging (with radiolabeled PET compounds) to calculate the % reduction in Aβ deposit in the brain of the patient before and after treatment. The SUVr values can be convened to standardized centiloid units, where 100 is average for AD and 0 is average for young controls, allowing comparability amongst amyloid PET tracers, and calculation of reduction according to centiloid units (Klunk et al., Alzheimers Dement, 2015; 11:1-15). As used herein, "a period of 6 months or less" refers to a period of time that is 6 months or less than 6 full consecutive calendar months, and wherein each month has 28-31 days. At the least this period includes a one-time induction dose given in a single administration.

A reduction or slowing of cognitive decline can be measured by cognitive assessments such as Clinical Dementia Rating—summary of boxes (CDR-SB). Mini-Mental State Exam (MMSE) or Alzheimer's Disease Assessment Scale-Cognitive (ADAS-Cog). A reduction or slowing of functional decline can be measured by functional assessments such as Alzheimer's Disease Cooperative Study-Activities of Daily Living (ADCS-ADL).

An "induction dose" is a dose of an anti-N3pGlu Aβ antibody that causes a sharp reduction in Aβ deposit in the brain of a human patient within 6 months of treatment. A "one-time" dose is an induction dose that is administered once to a patient. A "one-time" dose can also be a dose that is administered to a patient once with a prolonged period of time, such as 2-10 years, between doses if such a dose is needed. Whether a patients needs more than one "one-time" induction dose can be determined by a diagnostician or health care professional by using known techniques and by observing results. A "biweekly" dose is a dose of that is administered to a patient every two weeks.

A "maintenance dose" is a dose administered to a patient after the induction dose treatment. A maintenance dose is an amount of antibody or drug administered to maintain the desired therapeutic response including reduced Aβ deposit in the brain of a human patient. A maintenance dose can be dose that is the same or lower in amount of antibody or drug compared to the induction dose.

As used herein, "mg/kg" means an amount, in milligrams, of antibody or drug administered to a patient based on his or her body weight in kilograms. A dose is given at one time. For example, a 10 mg/kg dose of antibody for a patient weighing 70 kg would be a single 700 mg dose of antibody given in a single administration. Similarly, a 40 mg/kg dose of antibody for a patient weighing 80 kg would be a 3200 mg dose of antibody given at a single administration As used herein, the phrase "in combination with" refers to the administration of an anti-N3pGlu Aβ antibody of the present invention, with another molecule (a "combination molecule." such as a BACE inhibitor, symptomatic agent or Aβ antibody), simultaneously, or sequentially in any order, or any combination thereof. The two molecules may be administered either as part of the same pharmaceutical composition or in separate pharmaceutical compositions. The anti-N3pGlu Aβ antibody can be administered prior to, at the same time as, or subsequent to administration of the combination molecule, or in some combination thereof. Where the combination molecule is administered at repeated intervals (e.g. during a standard course of treatment), the anti-N3pGlu Aβ antibody can be administered prior to, at the same time as, or subsequent to, each administration of the combination molecule, or some combination thereof, or at different intervals in relation to therapy with the combination molecule, or in a single or series of dose(s) prior to, at any time during, or subsequent to the course of treatment with the combination molecule. One of ordinary skill in the art would recognize that a BACE inhibitor refers to a therapeutic agent, preferably a small molecule that inhibits the beta-secretase 1 enzyme, and can prevent the formation of amyloid plaque. Examples of BACE inhibitors are herein disclosed.

"Symptomatic agents,' as used herein refer to therapeutic agents used to treat the cognitive manifestations of Alzheimer's symptomatically and have not shown to have any effect on Alzheimer disease progression. These include acetyl cholinesterase inhibitors and NMDA receptor antagonists. The cholinesterase inhibitors approved for the management of AD symptoms include: donepezil (brand name Aricept™), galantamnine (Razadyne™), and rivastigmine (branded as Exelon and Exelon™ Patch). Memantine (also known as NAMEDA®) is an approved NMDA receptor antagonist. NAMZARIC® is a combination agent comprising both an acetyl cholinesterase inhibitor and NMDA receptor antagonist.

The following Examples and assays demonstrate that the antibodies of the present invention are useful for treating a disease characterized by deposition of Aβ, such as of Alzheimer's disease. Down's syndrome, and CAA. It should be understood however, that the following Examples are set forth by way of illustration and not limitation, and that various modifications may be made by one of ordinary skill in the art.

EXAMPLES

Example 1: Single Dose Efficacy in Aged Transgenic Mice

Single dose longitudinal effects of the murine surrogate mE8c anti-N3pGlu antibody (IgG2a) (U.S. Pat. No. 8,679, 498 B1) observed in aged PDAPP transgenic mice (18.5 to 20-months old). To mimic Aβ deposition rates and conditions in humans with Alzheimer's disease, mice are placed on a chow diet containing a BACE inhibitor LY2811376 (0.015%) four days prior to receiving a single intraperitoneal injection of biotinylated mE8c antibody or biotinylated control antibody of the same isotype, and remain on this diet for the duration of the study. A prior 4-month study demonstrated in aged PDAPP mice treated with the BACE inhibitor in feed resulted in a level of BACE inhibition that led to no change in the deposited Aβ over the 4-month interval (i.e. no further deposition and no clearance of deposited Aβ occurred). Animals are sacrificed 4, 8, 12, or 16 weeks after the single injection of biotinylated mE8c antibody (20 mg/kg or 100 mg/kg) or biotinylated control antibody (100 mg/kg) An additional control group of transgenic mice is sacrificed at study initiation (time zero cohort) and at 4, 8, 12, or 16 weeks (age matched control cohort). Hippocampus tissue is analyzed by acid urea gels to measure the Aβ1-42 via denaturing conditions.

Following the procedure essentially as described above, there was no significant difference in the levels of Aβ1-42 between the isotype control injected at 4, 8, 12, or 16-weeks (age matched control cohort) as compared to the time zero cohort. As such, the control animals were combined into one control group for comparison with animals injected with biotinylated mE8c antibody. Mice that received a single injection of 20 mg/kg biotinylated mE8c antibody had reduced levels of hippocampal Aβ1-42 as compared to control animals at 4-weeks (−6%), 8-weeks (−32% Dunnett's multiple comparison, p=0.0091), 12-weeks (−17%), and 16-weeks (−19%). The aged PDAPP mice that received a single injection of 100 mg/kg biotinylated mE8c antibody had reduced levels of hippocampal Aβ1-42 as compared to control animals at 4-weeks (−23%), 8-weeks (−28%; Dunnett's multiple comparison, p=0.0252), 12-weeks (−14%), and 16-weeks (−17%).

Example 2: Single Dose Target Engagement in Aged Transgenic Mice

To determine in-vivo target engagement of deposited plaque after a single dose of N3pGlu antibody, frozen hemi-brains from the single dose antibody study described in Example 1 are analyzed histologically to determine the percent area of hippocampus demonstrating antibody bound to plaque at 0, 4, 8, 12, and 16 weeks after a single dose of antibody.

Brains are sectioned and immunohistochemistry is performed on sister sections with an anti-human antibody (to detect the bound N3pGlu antibody) and 3D6 (to detect the total amount of deposited target in the section). Percent area bound by the N3pGlu antibody is normalized against the total amount of deposited target in the section.

Following procedures essentially as described above, the total area covered by deposited Aβ was not significantly different across all groups and the average hippocampal area covered by the stain varied from 27 to 39%. Little to no target engagement was observed for control animals. Significant target engagement was observed 4, 8, 12, and 16-weeks after the single dose of 20 mg/kg (2.8% (p<0.0001), 1.9% (p<0.0001), 1.1% (p=0.00$^3$), 0.6% (p=0.0323), respectively) or 100 mg/kg (5.5% (p<0.0001), 4.0% (p<0.0001), 2.6% (p<0.0001), 1.5% (p=0.0002), respectively) of biotinylated mE8c antibody (as compared to controls). Dunn non-parametric analysis was used to determine p-values. The average area of target engagement in mE8c-injected animals was highest after 4-weeks of treatment and the average target engagement decreased longitudinally at the subsequent 8, 12, and 16-week time points (1.9%, 1.1%, 0.6% respectively for the 20 mg/kg mE8c group, and 4.0%, 2.6%, and 1.5% respectively for the 100 mg/kg mE8c group). Due to the high level of variability, significant differences were not observed between the 20 and 100 mg/kg mE8c single dose injected animals for the matched time points except for week 12 and 16 (p-value=0.0465, 0.0432 unadjusted Wilcoxon).

Example 3: Single-Dose and Multiple-Dose, Dose-Escalation Clinical Trial for Alzheimer's Disease A phase I, double-blind, randomized, placebo-controlled, parallel-group, single-dose followed by multiple-dose, dose-escalation study in patients with MCI due to AD or mild-to-moderate AD was conducted to assess the safety, tolerability, and PK of single and multiple IV doses of LY3002813 (Antibody III). AD patients were enrolled into the single-ascending dose (SAD) phase and were each administered a single intravenous (IV) dose of Antibody III (5 dosing cohorts from 0.1 mg/kg IV to 10 mg/kg IV) or placebo followed by a 12-week follow-up period for each dose level. After the follow-up period, the same patients proceeded into the multiple-ascending dose (MAD) phase (5 cohorts) and were administered IV doses of Antibody III (0.3 mg-kg IV to 10 mg/kg IV) or placebo approximately once per month for up to 4 doses depending on the initial doses. This phase concluded with a 12-week follow-up period.

The results of the single-dose study, wherein the PK of Antibody III was assessed up to 84 days after a single dose, showed the mean terminal elimination half-life was approximately 4 days after single-dose administration from 0.1 mg/kg to 3.0 mg/kg, and was increased to approximately 10 days (243 hours) at the 10-mg/kg dose level. The mean clearance values at each dose level ranged from 26.3 mL/hour (10 mg/kg) to 35.6 mL/hour (1.0 mg/kg).

The results of the multiple-dose study, wherein patients entered the multiple-dose phase 12 weeks after receiving a single dose in the SAD phase, showed Antibody III concentrations were significantly lower following multiple doses of Antibody III than following the first single dose. In contrast to the other dose levels, at the 10-mg/kg dose level, Antibody III concentrations were generally similar to those observed after single-dose administration. Most patients at dose levels ≤3 mg/kg had serum Antibody III concentrations below the limits of detection 28 days after dosing. Patients receiving 10 mg/kg had sustained quantifiable concentrations 28 days after dosing.

Greater than 90% of the patients with AD had treatment-emergent antidrug antibodies (ADAs) 3 months after the first dose at all dose groups; titers tended to increase by the end of the MAD phase and persist 3 months after the last dose. The rapid decline of Antibody III concentrations after multiple-dose administration may be at least partly associated with the presence of ADAs. Treatment group also experienced increased infusion related reactions upon multiple dosing.

Florbetapir scans were performed at baseline and after the last MAD dose, separated by approximately 7 months. The change in whole grey matter standardized uptake value ratio (SUVr) with cerebellum as a reference region was compared across dose cohorts, and the SUVr values were convened to standardized centiloid (CL) units. There was a significant reduction in cerebral amyloid (as assessed by florbetapir PET imaging) in the 6 patients who received 3 to 5 doses of 10 mg/kg of Antibody III intravenously over 6 months, without cerebral vasogenic edema or microhemorrhage complications in this dose group. The mean reduction of 44 CL units corresponds to a mean 40-50% reduction in brain amyloid.

Florbetapir scans in extended follow up from three subjects treated with 3-5 doses of 10 mg kg IV of Antibody III (vs 2 placebo) demonstrated sustained amyloid removal 18 months after last dose. The data indicate that short term (and possibly single) dose of anti-N3pGlu Aβ antibodies (such as Antibody III) is sufficient to result in a sustained removal of amyloid. Chronic dosing with anti-N3pGlu Aβ antibodies is not required to maintain clearance of cerebral amyloid.

Example 4: Single-Dose and Multiple-Dose Clinical Trial for Alzheimer's Disease As a result of the significant target engagement (amyloid reduction by florbetapir PET) that was identified after 3 to 5 doses of LY3002813 (Antibody III) 10 mg/kg intravenously over 6 months, a Phase Ib study is in progress to confirm that different dosing regimens (single-dose, short-term "induction" dosing with higher, more frequent dosing; and chronic dosing for maximal PD effect) can mitigate immunogenicity and immune safety issues, and produce sustained amyloid reduction. A phase Ib, double-blind, randomized within cohort, placebo-controlled, parallel-group, single- and multiple-dose study in patients with MCI due to AD or mild-to-moderate AD is being conducted to assess the safety, tolerability, and PK of single and multiple IV doses of Antibody III. The study will be conducted in at least seven cohorts, including single IV doses at 10 mg/kg, 20 mg/kg, or 40 mg/kg (cohorts 1, 2, and 3, respectively), IV doses every two weeks for 24 weeks at 10 mg/kg or 20 mg/kg (cohorts 4 and 5, respectively), and IV doses every four weeks for up to 72 weeks at 10 mg/kg or 20 mg/kg (cohorts 6 and 7, respectively).

The primary target engagement outcome is the reduction of cerebral amyloid as measured by quantitative amyloid PET imaging (florbetapir CL) assessed at baseline and at 12 weeks, 24 weeks, 36 weeks, 48 weeks, and 72 weeks after starting treatment.

The results demonstrate that 10 mg/kg, 20 mg/kg and 40 mg/kg single doses and 10 mg/kg multiple doses of Antibody III can reduce amyloid at 12 weeks (mean reductions in cohorts to date ranging from −12 to −39 CL by florbetapir PET). For the patients who have had additional scans beyond 12 weeks, the amyloid clearance is sustained in the single dose cohorts, and further amyloid clearance is observed with dosing in the multiple dose cohort.

Example 5: Expression and Purification of Engineered N3pGlu Aβ Antibodies

Anti-N3pGlu Aβ antibodies of the present invention can be expressed and purified essentially as follows. An appropriate host cell, such as HEK 293 EBNA or CHO, is either transiently or stably transfected with an expression system for secreting antibodies using an optimal predetermined HC:LC vector ratio or a single vector system encoding both HC and LC. Clarified media, into which the antibody has been secreted, is purified using any of many commonly-used techniques. For example, the medium may be conveniently applied to a Protein A or G Sepharose FF column that has been equilibrated with a compatible buffer, such as phosphate buffered saline (pH 7.4). The column is washed to remove nonspecific binding components. The bound antibody is eluted, for example, by pH gradient (such as 0.1 M sodium phosphate buffer pH 6.8 to 0.1 M sodium Citrate buffer (pH 2.5). Antibody fractions are detected, such as by SDS-PAGE, and then are pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, or hydroxyapatite chromatography. The purity of the antibody after these chromatography steps is greater than 99%. The product may be immediately frozen at −70° C. or may be lyophilized. The amino acid sequences for the anti-N3pGlu Aβ antibodies are provided in Table A.

Example 6: Binding Affinity and Kinetics

The binding affinity and kinetics of anti-N3pGlu Aβ antibody of the present invention (Antibody I or Antibody II) to pE3-42 Aβ peptide or to Aβ 1-40 peptide is measured by surface plasmon resonance using BIACORE® 3000 (GE Healthcare). The binding affinity is measured by capturing the anti-N3pGlu Aβ antibody via immobilized protein A on a BIACORE® CM5 chip, and flowing pE3-42 Aβ peptide or Aβ 1-40 peptide, starting from 100 nM in 2-fold serial dilution down to 3.125 nM. The experiments are carried out at 25° C. in HBS-EP buffer (GE Healthcare BR 100669; 10 mM HEPES, 150 mM NaCl, 3 mM EDTA, 0.05% surfactant P20, pH 7.4).

For each cycle, the antibody is captured with 5 μL injection of antibody solution at a 10 μg/mL concentration with 10 μL/min, flow rate. The peptide is bound with 250 μL injection at 50 μL/min, and then dissociated for 10 minutes. The chip surface is regenerated with 5 μL injection of glycine buffer at pH 1.5 at 10 μL/mL flow rate. The data is fit to a 1:1 Langmiur binding model to derive $k_{on}$, $k_{off}$, and to calculate $K_D$. Following procedures essentially as described above, the following parameters (shown in Table C) were observed.

TABLE C

| Binding affinity and kinetics. | | | |
|---|---|---|---|
| Antibody | $k_{on}$ (×10$^5$ 1/MS) | $k_{off}$ (×10$^{-4}$ 1/s) | $K_D$ (nM) |
| I | 1.39 | 1.31 | 0.71 |
| II | 3.63 | 1.28 | 0.35 |
| III | 3.62 | 2.7 | 0.75 |
| IV | 4.03 | 3.72 | 0.92 |
| V | 5.78 | 3.21 | 0.55 |

No appreciable binding to Aβ 1-40 was detected, indicating that Antibodies I-V bound preferentially to pE3-42 Aβ peptide as compared to Aβ 1-40.

Example 7: Ex Vivo Target Engagement

To determine ex vivo target engagement on brain sections from a fixed PDAPP brain, immunohistochemical analysis is performed with an exogenously added anti-N3pGlu Aβ antibodies of the present invention (hE8L, B12L, R17L, Antibody I or Antibody II). Cryostat serial coronal sections from aged PDAPP mice (25-month old) are incubated with 20 μg/mL of an exemplified N3pGlu Aβ antibody of the present invention. Secondary HRP reagents specific for human IgG are employed and the deposited plaques are visualized with DAB-Plus (DAKO). Biotinylated murine 3D6 antibody followed by Step-HRP secondary is used as a positive control. The positive control antibody (biotinylated 3D6) labeled significant quantities of deposited Aβ in the PDAPP hippocampus, and the anti—N3pGlu Aβ antibodies (hE8L, B12L, R17L, Antibody 1 or Antibody II) labeled a subset of deposits. These histological studies demonstrated that the anti—N3pGlu Aβ antibodies of the present invention engaged deposited Aβ target ex vivo.

Example 8: Synthesis of N-[3-[(4aR,7aS)-2-Amino-6-(5-fluoropyrimidin-2-yl)-4,4a,5,7-tetrahydropyrrolo[3,4-d][3]thiazin-7a-yl]-4-fluoro-phenyl]-5-methoxy-pyrazine-2-carboxamide; Toluenesulfonic Acid

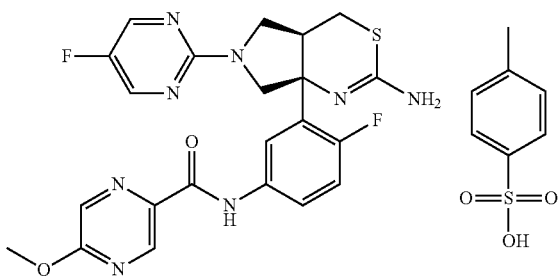

Crystalline Form 2 N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide hydrated (149.15 mg) is added to ethyl acetate (2 mL). The sample is stirred at 1000 rpm at a temperature of 80° C. p-Toluencsulfonic acid (70 mg dissolved in ethyl acetate (1 mL)) is added to the stirring solution, and it is stirred overnight at 80° C. to produce a slurry of a white solid which is isolated by vacuum filtration to provide the title compound.

Alternative Preparation A of N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide; Toluenesulfonic Acid N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide (9.5 g, 19 mmol) and p-toluenesulfonic acid (3.80 g, 19.8 mmol) are added to tetrahydrofuran (31 mL), water (7.9 mL), and 2-propanol (8.6 mL). The solution is heated to 40° C. To the warm solution is added 2-propanol (200.0 mL) over approximately 3 hours. The mixture is seeded shortly after the start of the 2-propanol addition with a portion of the title compound (500 mg, 0.75 mmol). After the solvent addition is complete, the mixture is cooled to approximately 20° C. over 1-3 hours. The mixture is heated from approximately 20° C. to approximately 55° C. over a target time of 2 hours. The temperature is held at 55° C. for 1 hour and then cooled to about 20° C. over approximately 4 hours. The slurry is stirred for at least 10 hours at approximately 20° C. The slurry is filtered and the wet cake is washed with water (57 mL). The product is dried in vacuo at 45° C. for at least 10 hours to give the title compound (10.4 g, 81%). ES/MS (m/z): 500 (M+H).

Alternative Preparation B of N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide; Toluenesulfonic Acid N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide hydrated (20.7 g) is slurried at 170 rpm in 60:40 THF:$H_2O$ (85 mL) in a 500 mL 3-necked round bottomed flask equipped with a nitrogen bubbler, IKA® mechanical motor/agitator attached to a glass shaft having a TEFLON® banana blade, and a thermocouple connected to a programmable J-KEM® temperature controller, p-Toluenesulfonic acid monohydrate (7.6 g, 1.03 eq) is dissolved in a mixture of 60:40 THF:$H_2O$ (20 mL) and the solution added all at once to the stirring N-[3-[(4aR,7aS)-2-amino-6-(5-fluoropyrimidin-2-yl)-4,4a, 5,7-tetrahydropyrrolo[3,4-d][1,3]thiazin-7a-yl]-4-fluoro-phenyl]-5-methoxy-pyrazine-2-carboxamide slurry at 23° C., leading almost immediately to a clear reddish tan solution. The agitation rate is then increased to 200 rpm as over 15 minutes, water (22 mL) is added to the solution, which is then seeded with N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide toluenesulfonic acid (750 mg, 3 wt % seed load) and is then stirred at 23° C. for a further 15 minutes. Over 6 hours, water (226 mL, total solvent of 353 mL; or 13.6 vol., final solvent ratio of 17.5:82.5 THF:$H_2O$) is added to the slurry, which is then stirred overnight (22 hours) at 23° C. The slurry is filtered via vacuum, rinsed with 15:85 THF:$H_2O$ (2×20 mL), then left on vacuum for 20 minutes while cracks which form in the product wet cake are manually pressed closed. The wet solids are dried at 40° C. under vacuum for about 72 hours to give the title compound as a white crystalline solid (24.07 g, 90.0 wt %).

The crystalline N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide; toluenesulfonic acid is characterized by an XRD pattern using CuKa radiation as having diffraction peaks (2-theta values) as described in Table D below, and in particular having peaks at diffraction angle 2-theta of 5.0° in combination with one or more of the peaks selected from the group consisting of 19.6°, 13.8°, and 18.5°; with a tolerance for the diffraction angles of 0.2 degrees.

TABLE D

X-ray powder diffraction peaks of crystalline Example 8

| Peak | Angle (2-Theta°) +/− 0.2° | Relative Intensity (% of most intense peak) |
|---|---|---|
| 1 | 5.0 | 100.0 |
| 2 | 13.4 | 22.9 |
| 3 | 13.8 | 37.3 |
| 4 | 14.4 | 20.2 |
| 5 | 15.3 | 28.8 |
| 6 | 17.5 | 25.9 |
| 7 | 18.5 | 30.7 |
| 8 | 19.6 | 45.8 |
| 9 | 20.4 | 17.7 |
| 10 | 25.6 | 30.1 |

Sequences
<SEQ ID NO: 1; PRT1; Artificial>
(HCDR1-Antibody I and Antibody II)
KASGYTFTDYYIN <SEQ ID NO: 2; PRT1; Artificial>
(HCDR2-Antibody I and Antibody II)
WINPGSGNTKYNEKFKG <SEQ ID NO: 3; PRT1; Artificial>
(HCDR3-Antibody I and Antibody II)
TREGETVY <SEQ ID NO: 4; PRT1; Artificial>
(LCDR1-Antibody I and Antibody II)
KSSQSLLYSRGKTYLN <SEQ ID NO: 5; PRT1; Artificial>
(LCDR2-Antibody II)
YAVSKLDS <SEQ ID NO: 6; PRT1; Artificial>
(LCDR2-Antibody I)
YDVSKLDS <SEQ ID NO: 7; PRT1; Artificial>
(LCDR3-Antibody I and Antibody II)
VQGTHYPFT <SEQ ID NO: 8; PRT1; Artificial>
(HCVR-Antibody I and Antibody II)
QVQLVQSGAEVKKPGSSVKVSCKASGYTFTDYYINWVRQAPGQGLEWMGW
INPGSGNTKYNEKFKGRVTITADESTSTAYMELSSLRSEDTAVYYCTREG
ETVYWGQGTLVTVSS <SEQ ID NO: 9; PRT1; Artificial>
(LCVR-Antibody I)
DVVMTQSPLSLPVTLGQPASISCKSSQSLLYSRGKTYLNWFQQRPGQSPR
RLIYDVSKLDSGVPDRFSGSGSGTDFTLKISRVEAEDVGVYYCVQGTHYP
FTFGQGTKLEIK <SEQ ID NO: 10; PRT1; Artificial>
(LCVR-Antibody II)
DIQMTQSPSTLSASVGDRVTITCKSSQSLLYSRGKTYLNWLQQKPGKAPK
LLIYAVSKLDSGVPSRFSGSGSGTEFTLTISSLQPDDFATYYCVQGTHYP
FTFGQGTKLEIK <SEQ ID NO: 11; PRT1; Artificial>
(HC-Antibody I and Antibody II)
QVQLVQSGAEVKKPGSSVKVSCKASGYTFTDYYINWVRQAPGQGLEWMGW
INPGSGNTKYNEKFKGRVTITADESTSTAYMELSSLRSEDTAVYYCTREG
ETVYWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPG <SEQ ID NO: 12; PRT1; Artificial>
(LC-Antibody I)
DVVMTQSPLSLPVTLGQPASISCKSSQSLLYSRGKTYLNWFQQRPGQSPR
RLIYDVSKLDSGVPDRFSGSGSGTDFTLKISRVEAEDVGVYYCVQGTHYP
FTFGQGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC <SEQ ID NO: 13; PRT1; Artificial>
(LC-Antibody II)
DIQMTQSPSTLSASVGDRVTITCKSSQSLLYSRGKTYLNWLQQKPGKAPK
LLIYAVSKLDSGVPSRFSGSGSGTEFTLTISSLQPDDFATYYCVQGTHYP
FTFGQGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC <SEQ ID NO: 14; DNA; Artificial>
Exemplified DNA for Expressing Antibody
Heavy Chain of SEQ ID NO: 11
CAGGTGCAGCTGGTGCAGTCTGGGGCTGAGGTGAAGAAGCCTGGGTCCTC
GGTGAAGGTCTCCTGCAAGGCTTCTGGATACACCTTCACCGACTATTATA
TCAACTGGGTGCGACAGGCCCCTGGACAAGGGCTTGAGTGGATGGGATGG
ATCAACCCTGGCAGTGGTAATACAAAGTACAATGAGAAGTTCAAGGGCAG
AGTCACGATTACCGCGGACGAATCCACGAGCACAGCCTACATGGAGCTGA
GCAGCCTGAGATCTGAGGACACGGCCGTGTATTACTGTACAAGAGAAGGC
GAGACGGTCTACTGGGGCCAGGGAACCCTGGTCACCGTCTCCTCAGCCTC
CACCAAGGGCCCATCGGTCTTCCCGCTAGCACCCTCCTCCAAGAGCACCT
CTGGGGGCACAGCGGCCCTGGGCTGCCTGGTCAAGGACTACTTCCCCGAA
CCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGG
TGACCGTGCCCTCCAGCAGCTTGGGCACCCAGACCTACATCTGCAACGTG
AATCACAAGCCCAGCAACACCAAGGTGGACAAGAAAGTTGAGCCCAAATC
TTGTGACAAAACTCACACATGCCCACCGTGCCCAGCACCTGAACTCCTGG
GGGGACCGTCAGTCTTCCTCTTCCCCCCAAAACCCAAGGACACCCTCATG
ATCTCCCGGACCCCTGAGGTCACATGCGTGGTGGTGGACGTGAGCCACGA
AGACCCTGAGGTCAAGTTCAACTGGTACGTGGACGGCGTGGAGGTGCATA
ATGCCAAGACAAAGCCGCGGGAGGAGCAGTACAACAGCACGTACCGTGTG
GTCAGCGTCCTCACCGTCCTGCACCAGGACTGGCTGAATGGCAAGGAGTA
CAAGTGCAAGGTCTCCAACAAAGCCCTCCCAGCCCCCATCGAGAAAACCA
TCTCCAAAGCCAAAGGGCAGCCCCGAGAACCACAGGTGTACACCCTGCCC
CCATCCCGGGACGAGCTGACCAAGAACCAGGTCAGCCTGACCTGCCTGGT
CAAAGGCTTCTATCCCAGCGACATCGCCGTGGAGTGGGAGAGCAATGGGC
AGCCGGAGAACAACTACAAGACCACGCCCCCCGTGCTGGACTCCGACGGC
TCCTTCTTCCTCTATAGCAAGCTCACCGTGGACAAGAGCAGGTGGCAGCA
GGGGAACGTCTTCTCATGCTCCGTGATGCATGAGGCTCTGCACAACCACT
ACACGCAGAAGAGCCTCTCCCTGTCTCCGGGT <SEQ ID NO: 15; DNA; Artificial>
Exemplified DNA for Expressing Antibody Light
Chain of SEQ ID NO: 12
GATGTTGTGATGACTCAGTCTCCACTCTCCCTGCCCGTCACCCTTGGACA
GCCGGCCTCCATCTCCTGCAAGTCTAGTCAAAGCCTCCTGTACAGTCGCG
GAAAAACCTACTTGAATTGGTTTCAGCAGAGGCCAGGCCAATCTCCAAGG
CGCCTAATTTATGATGTTTCTAAACTGGACTCTGGGGTCCCAGACAGATT
CAGCGGCAGTGGGTCAGGCACTGATTTCACACTGAAAATCAGCAGGGTGG
AGGCTGAGGATGTTGGGGTTTATTACTGCGTGCAAGGTACACACTACCCT
TTCACTTTTGGCCAAGGGACCAAGCTGGAGATCAAACGGACCGTGGCTGC
ACCATCTGTCTTCATCTTCCCGCCATCTGATGAGCAGTTGAAATCTGGAA
CTGCCTCTGTTGTGTGCCTGCTGAATAACTTCTATCCCAGAGAGGCCAAA -continued

```
GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGC
```

<SEQ ID NO: 16; DNA; Artificial>
Exemplified DNA for Expressing Antibody Light
Chain of SEQ ID NO: 13

```
GACATCCAGATGACCCAGTCTCCTTCCACCCTGTCTGCATCTGTAGGAGA

CAGAGTCACCATCACTTGCAAGTCCAGTCAGAGTCTCCTGTACAGTCGCG

GAAAAACCTATTTGAACTGGCTCCAGCAGAAACCAGGGAAAGCCCCTAAG

CTCCTGATCTATGCTGTCTCCAAACTGGACAGTGGGGTCCCATCAAGGTT

CAGCGGCAGTGGATCTGGGACAGAATTCACTCTCACCATCAGCAGCCTGC

AGCCTGATGATTTTGCAACTTATTACTGCGTGCAGGGTACACATTATCCT

TTCACTTTTGGCCAGGGGACCAAGCTGGAGATCAAACGGACCGTGGCTGC

ACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGC
```

<SEQ ID NO: 17; PRT1; Artificial>
(LCDR1-B12L/R17L/hE8L)
KSSQSLLYSRGKTYLN

<SEQ ID NO: 18; PRT1; Artificial>
(LCDR2-B12L/R17L/hE8L)
AVSKLDS

<SEQ ID NO: 19; PRT1; Artificial>
(LCDR3-B12L/R17L/hE8L)
VQGTHYPFT

<SEQ ID NO: 20; PRT1; Artificial>
(HCDR1-B12L)
GYDFTRYYIN

<SEQ ID NO: 21; PRT1; Artificial>
(HCDR1-R17L)
GYTFTRYYIN

<SEQ ID NO: 22; PRT1; Artificial>
(HCDR2-B12L/R17L/hE8L)
WINPGSGNTKYNEKFKG

<SEQ ID NO: 23; PRT1; Artificial>
(HCDR3-B12L)
EGITVY

<SEQ ID NO: 24; PRT1; Artificial>
(HCDR3-R17L)
EGTTVY

<SEQ ID NO: 25; PRT1; Artificial>
(LCVR-B12L/R17L)
DIVMTQTPLSLSVTPGQPASISCKSSQSLLYSRGKTYLNWLLQKPGQSPQ
LLIYAVSKLDSGVPDRFSGSGSGTDFTLKISRVEAEDVGVYYCVQGTHYP
FTFGQGTKLEIK <SEQ ID NO: 26; PRT1; Artificial> (HCVR-B12L)
QVQLVQSGAEVKKPGSSVKVSCKASGYDFTRYYINWVRQAPGQGLEWMGW
INPGSGNTKYNEKFKGRVTITADESTSTAYMELSSLRSEDTAVYYCAREG
ITVYWGQGTTVTVSS <SEQ ID NO: 27; PRT1; Artificial> (HCVR-R17L)
QVQLVQSGAEVKKPGSSVKVSCKASGYTFTRYYINWVRQAPGQGLEWMGW
INPGSGNTKYNEKFKGRVTITADESTSTAYMELSSLRSEDTAVYYCAREG
TTVYWGQGTTVTVSS <SEQ ID NO: 28; PRT1; Artificial> (LC-B12L/R17L)
DIVMTQTPLSLSVTPGQPASISCKSSQSLLYSRGKTYLNWLLQKPGQSPQ
LLIYAVSKLDSGVPDRFSGSGSGTDFTLKISRVEAEDVGVYYCVQGTHYP
FTFGQGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC <SEQ ID NO: 29; PRT1; Artificial> (HC-B12L)
QVQLVQSGAEVKKPGSSVKVSCKASGYDFTRYYINWVRQAPGQGLEWMGW
INPGSGNTKYNEKFKGRVTITADESTSTAYMELSSLRSEDTAVYYCAREG
ITVYWGQGTTVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPG <SEQ ID NO: 30; PRT1; Artificial> (HC-R17L)
QVQLVQSGAEVKKPGSSVKVSCKASGYTFTRYYINWVRQAPGQGLEWMGW
INPGSGNTKYNEKFKGRVTITADESTSTAYMELSSLRSEDTAVYYCAREG
TTVYWGQGTTVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPG N3pGlu Aβ (SEQ ID NO: 31)
[pE]FRHDSGYEVHHQKLVFFAEDVGSNKGAIIGLMVGGVVIA <SEQ ID NO, 32; PRT1; Artificial> (LCVR-hE8L)
DIVMTQTPLSLSVTPGQPASISCKSSQSLLYSRGKTYLNWLLQKPGQSPQ
LLIYAVSKLDSGVPDRFSGSGSGTDFTLKISRVEAEDVGVYYCVQGTHYP
FTFGQGTKLEIK <SEQ ID NO, 33; PRT1; Artificial> (LC-hE8L)
DIVMTQTPLSLSVTPGQPASISCKSSQSLLYSRGKTYLNWLLQKPGQSPQ
LLIYAVSKLDSGVPDRFSGSGSGTDFTLKISRVEAEDVGVYYCVQGTHYP
FTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE
VTHQGLSSPVTKSFNRGEC

<SEQ ID NO, 34; PRT1; Artificial> (HCVR-hE8L)
QVQLVQSGAEVKKPGSSVKVSCKAS<u>GYTFTDYYIN</u>VRQAPGQGLEWMG<u>W
INPGSGNTKYNEKFKG</u>RVTITADESTSTAYMELSSLRSEDTAVYYCAR<u>EG
ETVY</u>WGQTTVTVSS <SEQ ID NO, 35; PRT1; Artificial> (HC-hE8L)
QVQLVQSGAEVKKPGSSVKVSCKAS<u>GYTFTDYYIN</u>VRQAPGQGLEWMG<u>W
INPGSGNTKYNEKFKG</u>RVTITADESTSTAYMELSSLRSEDTAVYYCAR<u>EG
ETVY</u>WGQTTVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPG <SEQ ID NO: 36; PRT1; Artificial> (HCDR1-hE8L)
GYTFTDYYIN <SEQ ID NO: 37; PRT1; Artificial> (HCDR3-hE8L)
EGETVY <SEQ ID NO: 38; PRT1; Artificial> (Aβ 1-42)
DAEFRHDSGYEVHHQKLVFFAEDVGSNKGAIIGLMVGGVVIA <SEQ ID NO: 39; PRT1; Artificial>
(LCVR-Antibody VI)
MVSSAQFLFLLVLWIQETNGDVVMTQTPLTLSVTIGQPASISCKSSQSLL
YSDGKTYLNWLLQRPGQSPMRLIYLVSKLDSGVPDRFTGSGSGTDFTLKI
SRVEAEDLGVYYCVQGTHFPPTFGSGTKLEIKRADAAPTVSIFPP <SEQ ID NO: 40; PRT1; Artificial>
(HCVR-Antibody VI)
MGWSGVFLFLLSGTAGVHSEVQLQQSGPELVKPGASMKISCKASGYSFTG
YTMNWVKQSHGKNLEWIGLINPYSGVTRYNQKFKGKATLIVDKSSSTAYM
ELLSLTSEDSAVYYCTREAKREWDETYWGQGTLVTVSAAKTTPPSV <SEQ ID NO: 41; PRT1; Artificial>
(LCVR-Antibody VII)
MVSTAQFLFLLNLWIQETNGDVVMTQTPLTLSVTIGQPASISCKSSQSLL
YSDGKTYLNWLLQRPGQSPMRLIYLVSKLDSGVPDRFTGSGSGTDFTLKI
SRVEAEDLGVYYCVQGTHFPPTFGSGTKLEIKRADAAPTVSIFPPS <SEQ ID NO: 42; PRT1; Artificial>
(HCVR-Antibody VII)
MGWSGVFIFLLSGTAGVHSEVQLQQSGPELVKPGASMKISCKASGYSFTG
YTMNWVKQSHGKNLEWIGLINPYNGVTRYNQKFKGKATLIVDKSSSTAYM
ELLSLTSEDSAVYYCTREAKREWDETYWGQGTLVTVSAAKTTPPSVYPL <SEQ ID NO: 43; PRT1; Artificial>
(LCVR-Antibody VIII)
MKLPVRLLVLVFWIPVSSSDVVMTQTPLSLPVSLGDQASISCRSSQSLVH
SDGNTYLHWYLQKPGQSPKLLIYKVSNRFSGVPDRFSGSGSGTDFTLKIS
RVEAEDLGVYFCSQSTHVPPTFGGGTKLEIKRADAAPTVSIFPPSS <SEQ ID NO: 44; PRT1; Artificial>
(HCVR-Antibody VIII)
MDFGLSLLIFVLILKGVQCEVKLVESGGGLVQPGGSRKLSCAASGFTFSD
YGMAWVRQAPGKGPEWVAFISNLAYSIYYADTVTGRFTISRENAKNTLYL
EMSSLRSEDTAMYYCARYDYDNILDYVMDYWGQGTSVTVSSAKTTPPSVY
PL <SEQ ID NO: 45; PRT1; Artificial>
(LCVR-Antibody IX)
MKLPVRLLVLWIQETKGDVVLTQTPLTLSVTIGQPASISCKSSQSLLYSN
GKTYLNWLLQRPGQSPKRLIYVVSKLDSGVPDRFTGSGSGTDFTLKISRV
EAEDLGVYYCVQGTHFPFTFGSGTKLEIKRADAAPTVSIFPPSS <SEQ ID NO: 46; PRT1; Artificial>
(HCVR-Antibody IX)
MGWSGVFLFLLSVTEGVHSQVQLQQSGAELVRPGSSVKISCKASGYIFNN
YWINWVKQRPGQGLEWIGQIYPGDGDTNYNGKFKGKATLTADKSSSTAYM
QLSSLTSEDSAVYFCAREGYIVYWGQGTLVTVSAAKTTPPSVYPL <SEQ ID NO: 47; PRT1; Artificial>
(LCVR-Antibody X)
DVVMTQTPLSLPVSLGDQASISCRSSQSLLHSNGNTYLHWYLQKPGQSPK
LLIYKVSNRFSGVPDRFSGSGSGTDFTLKISRVEAEDLGVYFCSQSTHVP
LTFGAGT <SEQ ID NO: 48; PRT1; Artificial>
(HCVR-Antibody X)
QLQQSGAELMKPGASVKISCKATGYTFSSYWIEWVKQRPGHGLEWIGEIL
PGRGSTHYNEKFKGKATFTADTSSNTAYMQLSSLTSEDSAVYYCARSPIT
TSDYWGQGTTLTVSS <SEQ ID NO: 49; PRT1; Artificial>
(LCVR-Antibody XI)
SCRSSQSLVHSNGNTYLHWYLQKPGQSPKLLIYKVSNRFSGVPDRFSGSG
SGTDFTLKISRVEAEDLGVYFCSQSTHVPLTFGAGT <SEQ ID NO: 50; PRT1; Artificial>
(HCVR-Antibody XI)
AELKKPGASVKISCKATGYTFRSYWIEWVKQRPGHGLEWIGEILPGRGST
KYNEKFKGKATFTADTSSNTANMQLSSLTSEDSAVYYCARSPITTSDY <SEQ ID NO: 51; PRT1; Artificial>
(LCVR-Antibody XII)
DVVLTQTPFTLSVTIGQPASISCKSSQSLLHSNGESYLNWLFQRPGQSPK
RLIYAVSKLDSGVPDRFTGSGSGTDFTLKISRVEAEDLGVYYCVQGTHFP
FTFGGGTKLEIK <SEQ ID NO: 52; PRT1; Artificial>
(HCVR-Antibody XII)
QIQLQQSGPELVKPGAAVKISCKASGYTFTDYYLNWVKQKPGQGLEWIGW
IYPGSGNVKYNEKFKGKATLTADTSSNTAHMQLSSLTSEDTAVYFCTREG
LIVYWGQGTLVTVSA <SEQ ID NO: 53; PRT1; Artificial>
(LCVR-Antibody XIII)
DVVLTQTPLTLSVTIGQPASISCKSSQSLLYSNGKTYLNWLLQRPGQSPK
RLIYVVSKLDSGVPDRFTGSGSGTDFTLKISRVEAEDLGVYYCVQGTHYP
FTFGGGTKLEIK <SEQ ID NO: 54; PRT1; Artificial>
(HCVR-Antibody XIII)
QIQLQQSGPDLVKPGASVKISCKASGYTFTDYYINWVKQKPGQGLEWIGW

LNPGSGNTKYNEKFKGKATMTVDTTSSTVYMQLSSLTSEDSAVYFCTREG

PIDYWGRGTSVTVSS

<SEQ ID NO: 55; PRT1; Artificial>
(LCVR-Antibody XIV)
DIVMTQTPLSLSVTPGQPASISCSSSQSLIYSDGNAYLHWYLQKPGQSPQ

LLIYKVSNRFSGVPDRFSGSGSGTDFTLKISRVEAEDVGVYYCTQSTHSP

WTFGGGTKVEIK

<SEQ ID NO: 56; PRT1; Artificial>
(HCVR-Antibody XIV)
EVQLVESGGGLVKPGGSLRLSCAASGYTFSRYSMSWVRQAPGKGLEWVGQ

INIRGCNTYYPDTVKGRFTISRDDSKNTLYLQMNSLKTEDTAVYYCTTGD

FWGQGTLVTVSS

<SEQ ID NO: 57; PRT1; Artificial>
(LC-Antibody XV)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

<SEQ ID NO: 58; PRT1; Artificial>
(HC-Antibody XV)
QVQLVESGGGVVQPGRSLRLSCAASGFAFSSYGMHWVRQAPGKGLEWVAV

IWFDGTKKYYTDSVKGRFTISRDNSKNTLYLQMNTLRAEDTAVYYCARDR

GIGARRGPYYMDVWGKGTTVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PG

<SEQ ID NO: 59; PRT1; Artificial>
(LC-Antibody XVI)
DIVLTQSPATLSLSPGERATLSCRASQSVSSSYLAWYQQKPGQAPRLLIY

GASSRATGVPARFSGSGSGTDFTLTISSLEPEDFATYYCLQIYNMPITFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

<SEQ ID NO: 60; PRT1; Artificial>
(HC-Antibody XVI)
QVELVESGGGLVQPGGSLRLSCAASGFTFSSYAMSWVRQAPGKGLEWVSA

INASGTRTYYADSVKGRFTISRDNSKNTLYLQMNSLRAEDTAVYYCARGK

GNTHKPYGYVRYFDVWGQGTLVTVSSASTKGPSVFPLAPSSKSTSGGTAA

LGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSL

SLSPGK

<SEQ ID NO: 61; PRT1; Artificial>
(LC-Antibody XVII)
DIVMTQSPLSLPVTPGEPASISCRSSQSLVYSNGDTYLHWYLQKPGQSPQ

LLIYKVSNRFSGVPDRFSGSGSGTDFTLKISRVEAEDVGVYYCSQSTHVP

WTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

<SEQ ID NO: 62; PRT1; Artificial>
(HC-Antibody XVII)
EVQLVESGGGLVQPGGSLRLSCAASGFTFSSYGMSWVRQAPGKGLELVAS

INSNGGSTYYPDSVKGRFTISRDNAKNSLYLQMNSLRAEDTAVYYCASGD

YWGQGTTVTVSSASTKGPSVFPLAPCSRSTSESTAALGCLVKDYFPEPVT

VSWNSGALTSGVHTFPAVLQSSGLYSLSSVVTVPSSSLGTKTYTCNVDHK

PSNTKVDKRVESKYGPPCPPCPAPEFLGGPSVFLFPPKPKDTLMISRTPE

VTCVVVDVSQEDPEVQFNWYVDGVEVHNAKTKPREEQFNSTYRVVSVLTV

LHQDWLNGKEYKCKVSNKGLPSSIEKTISKAKGQPREPQVYTLPPSQEEM

TKNQVSLTCLVKGFYPSDIAVEWESNGQPENNYKTTPPVLDSDGSFFLYS

RLTVDKSRWQEGNVFSCSVMHEALHNHYTQKSLSLSLG

<SEQ ID NO: 63; PRT1; Artificial>
(LC-Antibody XVIII)
DVVMTQSPLSLPVTPGAPASISCRSSQSIVHSNGNTYLEWYLQKPGQSPK

LLIYKVSNRFSGVPDRFSGSGSGTDFTLRISRVEAEDVGIYYCFQGSHVP

PTFGPGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

<SEQ ID NO: 64; PRT1; Artificial>
(HC-Antibody XVIII)
EVQLVESGGGLVQPGGSLRLSCSASGFTFSSFGMHWVRQAPGKGLEWVAY

ISSGSSTIYYGDTVKGRFTISRDNAKNSLFLQMSSLRAEDTAVYYCAREG

GYYYGRSYYTMDYWGQGTTVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

-continued

REPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLSL

SPGK

<SEQ ID NO: 65 PRT1; Artificial>
(LC-Antibody XIX)
DVVMTQSPLSLPVTLGQPASISCRSSQSLIYSDGNAYLHWFLQKPGQSPR

LLIYKVSNRFSGVPDRFSGSGSGTDFTLKISRVEAEDVGVYYCSQSTHVP

WTFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

<SEQ ID NO: 66; PRT1; Artificial>
(HC-Antibody XIX)
EVQLVESGGGLVQPGGSLRLSCAASGFTFSRYSMSWVRQAPGKGLELVAQ

INSVGNSTYYPDTVKGRFTISRDNAKNTLYLQMNSLRAEDTAVYYCASGD

YWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISR

TPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFF

LYSKLTVDKSRWQQGNVFSCSVMHEALHNHYTQKSLSLSPGK

---

We claim:

1. A method of reducing amyloid beta (Aβ) deposits in the brain of a human patient in need thereof comprising:
    administering to the patient more than one intravenous doses of 3 to 60 mg/kg of an anti-N3pGlu Aβ antibody at a frequency of no more than one dose of the anti-N3pGlu Aβ antibody every four weeks
    wherein the anti-N3pGlu Aβ antibody comprises a light chain variable region (LCVR) and a heavy chain variable region (HCVR), wherein the LCVR consists of SEQ ID NO: 25 and the HCVR consists of SEQ ID NO: 26
    e).

2. The method according to claim 1, wherein the anti-N3pGlu Aβ antibody comprises a light chain (LC) and a heavy chain (HC), wherein said LC consists of SEQ ID NO: 28 and HC consists of SEQ ID NO: 29
    e).

3. The method according to claim 1, wherein at least 3 doses of the anti-N3pGlu Aβ antibody are administered at a frequency of no more than one dose of the anti-N3pGlu Aβ antibody every 4 weeks.

4. The method according to claim 1, wherein the human patient is suffering from: i) preclinical or clinical Alzheimer's disease (AD), ii) Down's syndrome, or iii) clinical or pre-clinical cerebral amyloid angiopathy.

5. The method according to claim 1, wherein the human patient is suffering from preclinical AD, prodromal AD, mild AD, moderate AD, or severe AD.

6. The method according to claim 1, wherein the dose of the anti-N3pGlu Aβ antibody administered to the patient is 10 to 40 mg/kg.

7. The method according to claim 1, wherein the dose of the-anti-N3pGlu Aβ antibody administered to the patient is 3 to 20 mg/kg.

8. The method according to claim 1, wherein the induction dose of the anti-N3pGlu Aβ antibody administered to the patient is 15 to 30 mg/kg.

9. The method according to claim 1, wherein the dose of the anti-N3pGlu Aβ antibody administered to the patient is selected from 3 mg/kg, 10 mg/kg, 15 mg/kg, 20 mg/kg, and 40 mg/kg.

10. The method according to claim 1, wherein the dose of the anti-N3pGlu Aβ antibody administered to the patient is 10 mg/kg.

11. The method according to claim 1, wherein the dose of the anti-N3pGlu Aβ antibody administered to the patient is 20 mg/kg.

12. The method according to claim 1, wherein the dose of the anti-N3pGlu Aβ antibody administered to the patient is 40 mg/kg.

13. The method according to claim 1, wherein the administered dose and frequency are sufficient to provide a sustained reduction in Aβ deposits in the brain of the human patient for at least 18 months.

14. The method according to claim 1, wherein the administered dose and frequency are sufficient to reduce the level of Aβ deposits in the brain of the human patient by 35-100% within 6 months of administration of a first dose of the anti-N3pGlu Aβ antibody.

15. The method according to claim 1, wherein the method comprises administering to the human patient a 700 mg dose of the anti-N3pGlu Aβ antibody.

16. The method according to claim 15, wherein the method comprises administering to the human patient 3-5 doses of the anti-N3pGlu Aβ antibody over a period of 6 months or less.

17. The method according to claim 1, wherein the method comprises administering to the human patient 3-5 doses of 700 mg of the anti-N3pGlu Aβ antibody over a period of 6 months or less, wherein the administered dose and frequency are sufficient to provide a sustained reduction in Aβ deposits in the brain of the patient for at least 18 months.

18. The method according to claim 1, wherein the method comprises administering to the human patient 3-5 doses of 700 mg of the anti-N3pGlu Aβ antibody over a period of 6 months or less, wherein the administered dose and frequency are sufficient to reduce the level of Aβ deposits in the brain of the patient by 35-100% within 6 months of administration of a first dose of the anti-N3pGlu Aβ antibody.

* * * * *

UNITED STATES PATENT AND TRADEMARK OFFICE
CERTIFICATE OF CORRECTION

PATENT NO. : 11,312,763 B2
APPLICATION NO. : 16/310629
DATED : April 26, 2022
INVENTOR(S) : Ronald Bradley Demattos et al.

It is certified that error appears in the above-identified patent and that said Letters Patent is hereby corrected as shown below:

On the Title Page

Column 2 (Item (56) Other Publications) Line 5 Delete "Durgs" and insert -- Drugs --.

In the Claims

Column 111 Line 31-32 In Claim 1, delete "26 e)." and insert -- 26. --.

Column 111 Line 36-37 In Claim 2, delete "29 e)." and insert -- 29. --.

Column 111 Line 52 In Claim 7, delete "the-anti-" and insert -- the anti- --.

Column 111 Line 54 In Claim 8, after "the" delete "induction".

Signed and Sealed this
Twenty-fifth Day of October, 2022

Katherine Kelly Vidal
*Director of the United States Patent and Trademark Office*